(12) United States Patent
Elizazu et al.

(10) Patent No.: US 9,453,838 B2
(45) Date of Patent: Sep. 27, 2016

(54) METHODS FOR MAKING MICROARRAYS AND THEIR USES

(71) Applicant: Asociación Centro De Investigación Cooperative En Bioma Teriales, Gipuzkoa (ES)

(72) Inventors: Ana Beloqui Elizazu, Gipuzkoa (ES); Neils-Christian Reichardt, Gipuzkoa (ES)

(73) Assignee: Asociación Centro de Investigación Cooperative en Biomateriales, Sebastian, Guipuzcoa (ES)

( * ) Notice: Subject to any disclaimer, the term of this patent is extended or adjusted under 35 U.S.C. 154(b) by 37 days.

(21) Appl. No.: 14/203,611

(22) Filed: Mar. 11, 2014

(65) Prior Publication Data

US 2014/0274771 A1 Sep. 18, 2014

Related U.S. Application Data

(60) Provisional application No. 61/777,202, filed on Mar. 12, 2013.

(51) Int. Cl.
| | |
|---|---|
| *G01N 33/531* | (2006.01) |
| *G01N 33/543* | (2006.01) |
| *C40B 50/18* | (2006.01) |

(52) U.S. Cl.
CPC ......... *G01N 33/54353* (2013.01); *C40B 50/18* (2013.01); *G01N 33/531* (2013.01); *G01N 33/543* (2013.01); *G01N 2610/00* (2013.01)

(58) Field of Classification Search
None
See application file for complete search history.

(56) References Cited

U.S. PATENT DOCUMENTS

| 6,020,208 A | 2/2000 | Hutchens et al. |
|---|---|---|
| 2010/0004137 A1 | 1/2010 | Mrksich et al. |

OTHER PUBLICATIONS

Beloqui, Ana et al., "A surface-based mass spectrometry method for screening glycosidase specificity in environmental samples", Chem. Commun., 48: 1701-1703 (2012).
Bermudez, Victor M. et al., "Functionalization of Indium Tin Oxide", Langmuir, 22: 11113-11125 (2006).
Carlson, Erin E., "Chemoselective probes for metabolite enrichment and profiling", Nature Methods (2007).
Chang, Shih-Huang et al., "Glycan Array on Aluminum Oxide-Coated Glass Slides through Phosphonate Chemistry", JACS, 132: 11371-11380 (2010).

(Continued)

*Primary Examiner* — Karen S Weiler
(74) *Attorney, Agent, or Firm* — Patrick J. Hagan; Dann, Dorfman, Herrell and Skillman, P.C.

(57) ABSTRACT

The present invention provides microarrays that can be analysed by more than one technique using a non-covalent ligand attachment strategy to solid supports such as indium tin oxide (ITO) covered transparent glass slides. This provides, inter alia, glycan arrays on a micrometer scale which allow multimodal readout by MALDI-Tof-MS, fluorescence and optical microscopy. Glycans functionalized with a C5-aminolinker were attached in situ on a picomolar scale to a hydrophobic tag bound to this surface, thus avoiding the wasteful off-chip ligand tagging of other approaches. Glycan arrays prepared using this methodology were analysed both with a fluorescence scanner and by on-chip MALDI-mass spectrometry in a series of glycomics experiments specifically requiring a multimodal readout.

27 Claims, 16 Drawing Sheets

(56) References Cited

OTHER PUBLICATIONS

Fang, Aiping et al., "Anchoring of Self-Assembled Hemoglobin Molecules on Bare Indium—Tin Oxide Surfaces", Langmuir, 17: 4360-4366 (2001).
Gurard-Levin, Zachary A. et al., "High-Throughput Screening of Small Molecule Libraries using SAMDI Mass Spectrometry", ACS Comb. Sci., 137: 347-350 (2011).
Imming, Peter et al., "Drugs, their targets and the nature and number of drug targets", Nature Reviews Drug Discovery, 5: 821-834 (2006).
Jonkheijm, Pascal et al., "Chemical Strategies for Generating Protein Biochips", Angew. Chem. Int. Ed., 47: 9618-9647 (2008).
Kepper, Pamela et al., "Matrix-Assisted Laser Desorption/Ionization Mass Spectrometric Analysis of DNA on Microarrays", Clinical Chemistry, 52(7): 1303-1310 (2006).
Koster, Hubert et al., "A strategy for rapid and efficient DNA sequencing by mass spectrometry", Nature Biotechnology, 14: 1123-1128 (1996).
O'Donnell, Maryanne J. et al., "High-Density, Covalent Attachment of DNA to Silicon Wafters for Analysis by MALDI-TOF Mass Spectrometry", Anal. Chem., 69: 2438-2443 (1997).
Odendaal, Antoinette Y. et al., "Chemoselective enrichment for natural products discovery", Chem. Sci., 2: 760-764 (2011).
Pantazaki, A.A. et al., "Biotechnologically relevant enzymes from Thermus thermophilus", Appl. Microbiol. Biotechnol., 58: 1-12 (2002).
Ramakrishnan, Boopathy et al., "α-Lactalbumin (LA) Stimulated Milk β-1,4-Galactosyltransferase I (B4Gal-T1) to Transfer Glucose from UDP-glucose to N-Acetylglucosamine", The Journal of Biological Chemistry, 276(40): 37665-37671 (2001).
Sanchez-Ruiz, Antonio et al., "MALDI-TOF Mass Spectrometric Analysis of Enzyme Activity and Lectin Trapping on an Array of N-Glycans", Angeew. Chem. Int. Ed., 50: 1-5 (2011).
Serna, Sonia et al., "Construction of N-glycan Microarrays by Using Modular Synthesis and On-Chip Nanoscale Enzymatic Glycosylation", Chem. Eur. J., 16: 13163-13175 (2010).
Serna, Sonia et al., "Fucosyltransferases as Synthetic Tools: Glycan Array Based Substrate Selection and Core Fucosylation of Synthetic N-Glycans", JACS, 133: 16495-16502 (2011).
Su, Jing et al., "Using Mass Spectrometry to Characterize Self-Assembled Monolayers Presenting Peptides, Proteins, and Carbohydrates", Angew. Chem. Int. Ed., 41(24): 4715-4718 (2002).
Veinot, Jonathan G.C. et al., "Toward the Ideal Organic Light-Emitting Diode. The Versatility and Utility of Interfacial Tailoring by Cross-Linked Siloxane Interlayers", Acc. Chem. Res., 38: 632-643 (2005).
Reichardt, Niels-Christian, "Array Based Glycomics: Tools and Applications", International Carbohydrate Symposium, Madrid, Jul. 25, 2012.
Elizazu, Ana Beloqui, "Glycan Arrays on Ito-Slides for Maldi-TOF MS, Fluorescence and Optical Readout", International Carbohydrate Symposium, Madrid, Jul. 25, 2012.
Elizazu, Ana Beloqui, Glycan Arrays on Ito-Slides for Maldi-TOF MS, Fluoresence and Optical Readout, Inventors' Institute, San Sebastian, Jul. 2012.

| Ligand | SURFACE A | | | | | SURFACE B | | | | | | | |
|---|---|---|---|---|---|---|---|---|---|---|---|---|---|
| | GalT | CeGalNAcT | CeFuT6 | GalT + CeFuT6 | CeFuT8 | GalT | GalT + SialT | CeGalNAcT | CeFuT1 | CeFuT6 | CeFuT8 | AtFuTA | AgFuT6 |
| GL1 | 0 | 0 | 25 | 24 | 0 | 0 | 0 | 0 | 0 | 58 | 0 | 0 | 0 |
| GL2 | 0 | 0 | 56 | 59 | 0 | 0 | 0 | 0 | 72 | 100 | 0 | 0 | 0 |
| GL3 | 0 | 0 | 0 | 0 | 0 | 0 | 0 | 0 | 78 | 0 | 0 | 0 | 0 |
| GL4 | 0 | 0 | 0 | 0 | 0 | 0 | 0 | 0 | 0 | 0 | 0 | 0 | 0 |
| GL5 | 0 | 0 | 0 | 0 | 0 | 0 | 0 | 0 | 64 | 0 | 0 | 0 | 0 |
| GL6 | 0 | 0 | 0 | 0 | 0 | 0 | 0 | 0 | 0 | 0 | 0 | 0 | 0 |
| GL7 | 15 (m), 78 (d) | 54 (m), 15 (d) | 0 | 17 (m) | 0 | 9 (m), 65 (d) | nd | 48 (d) | 0 | 0 | 0 | 0 | 0 |
| GL8 | 93 (d) | 32 (m), 23 (d) | 2 | 25 (m), 10 (d) | 30 | 6, 94 | 31 (m), 12 (d) | 21 (m), 47 (d) | 0 | 40 | 62 | 31 | 55 |
| GL9 | 100 | 54 (m), 11 (d) | 0 | 24 (m), 7 (d) | 22 | 100 | 24 (m), 8 (d) | 32 (m), 29 (d) | 0 | 0 | 58 | 80 | 43 |
| GL10 | 92 | 49 | 33 | 32 (m), 51 (d) | 34 | 100 | 100 | 75 | 0 | 77 | 79 | 65 | 81 |
| GL11 | 82 (t) | 30 (m), 14 (d), 4 (t) | 0 | 18 (m) | 0 | 11 (d), 89 (t) | 41 (m) | 19 (m), 12 (d), 17 (t) | 0 | 0 | 0 | 78 | 0 |
| GL12 | 88 (t) | 32 (m), 20 (d), 2 (t) | 0 | 15 (m), 6 (d) | 17 | 8 (d), 92 (t) | 18 (m), 8 (d) | 18 (m), 25 (d), 21 (t) | 0 | 0 | 60 | 19 | 54 |
| GL13 | 100 | 34 (m), 20 (d), 3 (t) | 0 | nd | 0 | 7 (m), 7 (d), 9 (t), 77 (te) | 32 (m) | 14 (m), 14 (d), 10 (t), 7 (te) | 0 | 0 | 0 | 0 | 0 |
| GL14 | 86 | 100 | 0 | 35 (m) | 34 | 82 | 28 | 82 | 0 | 0 | 43 | 82 | 75 |
| GL15 | 85 | 67 | 0 | 46 (m) | 52 | 82 | 45 | 65 | 0 | 0 | 93 | 92 | 82 |
| GL16 | 100 | 72 | 0 | 49 (m) | 33 | 83 | 47 | 81 | 0 | 0 | 90 | 85 | 79 |
| GL17 | 97 | 50 | 0 | 45 (m) | 27 | 79 | 52 | 68 | 0 | 0 | 0 | 87 | 81 |
| GL18 | 0 | 0 | 15 (m), 7 (d) | 18 (m), 7 (d) | 0 | 0 | 17 (m), 6 (d) | 0 | 0 | 32 (m), 8 (d) | 0 | 0 | 0 |

FIG. 16

METHODS FOR MAKING MICROARRAYS AND THEIR USES

FIELD OF THE INVENTION

The present invention relates to methods for making microarrays, microarrays as obtainable by using the methods and methods of analysing test samples to determine whether one or more components of a test sample are capable of interacting with the microarray, in particular through the use of mass spectroscopy or the use of a plurality of analytical techniques.

BACKGROUND OF THE INVENTION

Microarrays are now a commonly used format for most high-throughput screening applications in genomics, proteomics and glycomics and the ability to analyse them by more than a single readout method is desirable to broaden their applications. While the first examples to couple affinity-chromatography with MALDI-Tof MS employed off-line isolation of analytes onto blotting membranes or functionalized beads, the advantages of directly functionalizing the MALDI sample plate were rapidly recognized. The covalent attachment of capture molecules to the sample plate has allowed the observation of antibody-antigen, protein-protein, lectin-carbohydrate interactions or the sequencing of captured oligonucleotides by MALDI-Tof MS. With a cleavable linkage to the surface, any enzymatic or chemical transformation leading to a mass change on the immobilized substrates can be observed directly by MALDI-Tof MS. Detachment of the immobilized analytes from the sample plate under laser irradiation have been achieved via photocleavable linkers, thiolates that desorb under laser irradiation or non-covalent fluorous and hydrophobic interactions.

However, the mass spectrometric analysis of microarrays, particularly those with small spot sizes (e.g., between 100-600 µm in diameter) has been hampered by constraints in method sensitivity and fabrication and efforts in this direction were limited to commercial well plate formats or slides with manually-deposited binding agent.

Glycan microarrays have advanced our understanding of carbohydrate-protein interaction and the associated field of glycomics like no other high-throughput technology. Thousands of individual carbohydrate binding events can be observed at the same time with often attomolar receptor sensitivity and, perhaps more important, using only picomolar amounts of glycan ligands. Most glycan array studies have focused on the analysis of substrate specificities of carbohydrate binding proteins, the study of cell surface receptors in bacteria and eukaryotic cell lines or the measurement of substrate specificities of selected glycosyltransferases employing fluorescent readout methods.

The on-chip activity screening of carbohydrate processing enzymes (glycosyltransferases, hydrolases, transglycosidases etc.) has important applications like the discovery of new glycosyltransferases, the evaluation of substrate specificities of biomass degrading enzymes, specificities of carbohydrate modifying enzymes like sulfatases, acylases, kinases etc., the rapid screening of potential inhibitors against a specific enzyme target or monitoring the outcome of on-chip enzymatic synthesis. In these cases, the use of fluorescently tagged probes or substrates only provides qualitative information and, furthermore, a ranking of ligands is often compromised by low individual binding strengths between ligand and affinity probe.

Several groups have picked up on the pioneering work of Mrksich (Su and Mrksich, 2002) to analyse surface bound glycans and other biomolecules by MALDI-TOF mass spectrometry. Due to constrains in fabrication and method sensitivity these surface-based mass spectrometry studies were carried out at the macroscopic scale using commercial samples with well dimensions of around 5 mm or manually spotted larger spots (Su and Mrksich, 2002; Sanchez-Ruiz et al., 2011; Chang et al. 2010). Microarrays, however, present spot sizes at least 10 times smaller in the range of 200-800 µm, which are resolved with a resolution of 5-10 µm by a standard slide scanner.

Sanchez-Ruiz et al. 2011 describes the use of MALDI-Tof mass spectroscopic analysis of enzyme activity using glycan arrays formed gold surfaces using a method which involves initially functionalising glycans with lipid tags and then non-covalently immobilising them on alkylthiolate SAM on a MALDI-Tof plate. Glycan arrays made using a similar approach are disclosed in Beloqui et al. 2012 and used for screening glycosidase specificity in environmental samples.

US Patent Application No: 2010/0004137 (Mrksich et al.) describes biochips with gold surfaces on which self-assembled monolayers (SAMs) of alkanethiol molecules are covalently attached via thiol chemistry. Glycans are immobilised on the biochips through reaction with terminal oligo (ethylene glycol) groups provided on the alkanethiol molecules so that they become covalently linked to the biochip and studied using MALDI-Tof spectroscopy.

Chang et al. 2010 makes glycan arrays in which the glycans are covalently or non-covalently attached to aluminium oxide coated glass (ACG) slides. For non-covalent attachment, the glycans are initially tagged with polyfluorinated hydrocarbon tails and then spotted robotically onto the ACG slide surface containing a layer of polyfluorinated hydrocarbon terminated with phosphonate. For covalent attachments, the glycans with a phosphonic acid tail were synthesized and spotted robotically onto the ACG slide surface. The non-covalent array was characterized by MS-Tof via ionization/desorption at a low laser energy without addition of matrix.

There remains a need in the art to further develop microarrays, and in particular to develop efficient ways of making arrays and/or to develop arrays capable of providing multimodal readout.

SUMMARY OF THE INVENTION

Broadly, the present invention is based on the realisation that strategies in which glycan molecules used to form a microarray are pre-tagged, e.g. with lipid or hydrocarbon tail groups, before being immobilised at locations in the microarray are wasteful and time-consuming, ultimately limiting the scale and degree of miniaturisation that can be achieved in the synthesis of the microarray. In addition, the present inventors realised that it would be advantageous if microarrays could be analysed using more than one technique. Based on a non-covalent ligand attachment strategy and indium tin oxide (ITO) covered transparent glass slides as a solid support, the present invention provides, inter alia, glycan arrays on a micrometer scale which allow multimodal readout by MALDI-Tof-MS, fluorescence and optical microscopy. Glycans functionalized with a C5-aminolinker were attached in situ on a picomolar scale to a hydrophobic tag bound to this surface, thus avoiding the wasteful off-chip ligand tagging of other approaches. Glycan arrays prepared using this methodology were analysed both with a fluorescence scanner and by on-chip MALDI-mass spectrometry in a series of glycomics experiments specifically requiring a multimodal readout.

In the examples herein, results are provided of experiments in which the specificity of various glycosyltransferases on an N-glycan microarray by incubation both with selected lectins and by MALDI-Tof and MS/MS analysis setting the basis for the on-chip enzymatic synthesis of large glycan libraries. Similarly, different glycoforms of a protein trapped on an array of lectins are differentiated and analysed and the trapping, digestion and identification of a lectin by sequence homology bound to a glycan microarray.

The possibility to interrogate biochips in general, and glycan chips in particular, by more than a single readout method using the same format broadens the range of applications, permits the confirmation of results through an independent method, maximizes the utility of the valuable biochips and, in the case of mass spectrometry, provides structural information on the present analytes. Examples are the use of combined mass spectrometry and fluorescence readout for the massive parallel on-chip glycan synthesis and subsequent interrogation of glycan function. The use of different readout methods with different sensitivity (like e.g. mass spectrometry and fluorescence) on the same chip however can have important implications for the chip design.

Accordingly, in a first aspect, the present invention provides a method of making a microarray on a surface of a solid substrate, the method comprising:
(a) providing a solid substrate having a surface for immobilizing a plurality of binding agents for forming the microarray;
(b) forming a support layer of hydrophobic molecules attached to the surface;
(c) forming a layer of linker molecules on the surface of the substrate, wherein the linker molecules comprise a hydrophobic group capable of non-covalently binding to the support layer and a reactive functional group; and
(d) printing a plurality of binding agents at a plurality of locations on the solid substrate, wherein the binding agents comprise a functional group capable of reacting in situ on the microarray with the reactive functional group of the linker molecules to covalently link the binding agents to the linker molecules immobilized on the solid substrate, thereby forming the microarray.

In a further aspect, the present invention provides a microarray as obtainable by a method as described herein.

In a further aspect, the present invention provides a method of analysing a test sample to determine whether one or more components of the test sample are capable of interacting with a binding agent in the microarray as obtainable by the method of as described herein, the method comprising:
(a) applying a test sample to the microarray so that components of the test sample are capable of interacting with the binding agents to the locations in the microarray; and
(b) detecting whether one or more components of the test sample interact with the binding agent immobilized at one or more locations in the microarray.

In a further aspect, the present invention provides a method of analysing a test sample to determine whether one or more components of the test sample are capable of interacting with a binding agent in a microarray formed on the surface of a solid substrate, wherein the microarray comprises:
(i) a solid substrate having a surface covalently linked to a support layer comprising a self-assembled monolayer (SAM) of hydrophobic molecules;
(ii) a layer of linker molecules comprising hydrophobic groups capable of non-covalently binding to the support layer; and
(iii) a plurality of binding agents at a plurality of locations on the solid substrate, wherein the binding agents are covalently linked to the linker molecules, thereby immobilizing the binding agents at the locations on the surface;

the method comprising:
(a) applying a test sample to the microarray so that components of the test sample are capable of interacting with the binding agents to the locations in the microarray; and
(b) detecting whether one or more components of the test sample interact with the binding agent immobilized at one or more locations in the microarray.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIG. 3A) Spot diameters for glycans spotted at 1.2 pmol. FIG. 3B) Spot diameters for the indicated spotted amounts of glycan G9.

FIG. 4A) Schematic representations of analyzed C5-amino-glycans. FIG. 4B) Fluorescently labelled lectins BSL-II, RCA and AAL were used to detect analytes spotted at the indicated concentrations.

FIG. 11A) MALDI-Tof MS of GL10_Gal compound after treatment with CeFuT6 enzyme. FIG. 11B) Structures 2 and 3 were determined by MALDI-Tof/Tof analysis of peaks 2 and 3. FIG. 11C) Mass list from LIFT spectra. Masses important for the determining structures 2 and 3 are indicated.

FIG. 16. Conversion yields (%) for the GL1-GL18 with glycosyl transferase enzymes on surfaces A and B. nd=not determined; (m)=mono-, (d) di-, (t) tri- and (te) tetra-glycosyltransferred reaction products.

DETAILED DESCRIPTION

Glycans

Figure 1:
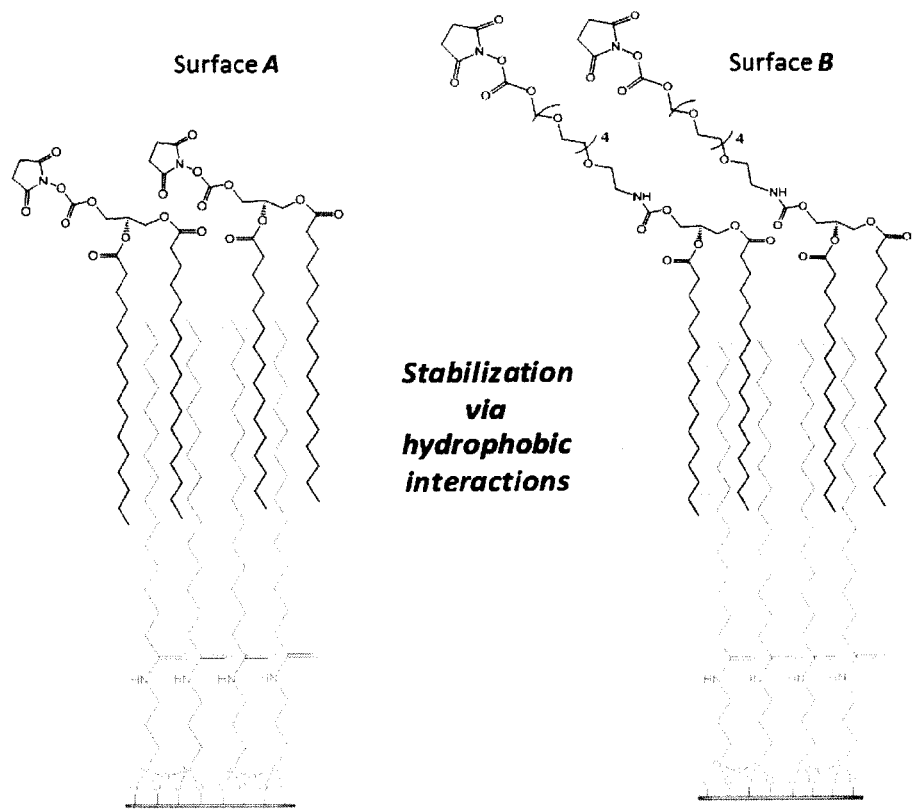
FIG. 1. Schematic representation of surfaces A and B. ITO slides silanized with 3-aminopropyl trietoxysilane and treated with N-succinimidyl stearic acid were subsequently overlayed with bidentate linker compounds 1 (to form surface A) or 2 (to form surface B). Surface-stabilising hydrophobic interactions between stearic acid and bidentate linker tails are indicated.

The term glycan includes any saccharide (mono-, oligo- or poly-) in free form or forming a carbohydrate portion of a glycoconjugate molecule such as a glycoprotein, proteoglycan or glycolipid. Glycans are important molecules involved in virtually every biological structure and process. Constituent monosaccharides generate a much greater combinatorial diversity than nucleic or amino acids, and further diversity arises from covalent modification of glycans. The total glycan repertoire (glycome) of a given organism is thus much more complex and dynamic than the genome or proteome.

Linkages between monosaccharides can be in $\alpha$- or $\beta$-form, chains can be linear or branched and glycan modifications include acetylation and sulfation. Glycoproteins carry one or more glycan covalently attached to a polypeptide via N or O linkages.

O-glycans are linked to hydroxyl groups of serine or threonine residues. N-glycans are sugar chains linked via a side-chain nitrogen (N) to an asparagine residue. They share a common pentasaccharide region of two mannose residues, linked separately by $\alpha$1-3 and $\alpha$1-6 linkages to a central mannose, which in turn is linked by a $\beta$1-4 linkage to a chitobiose core consisting of two $\beta$1-4-linked GlcNAc residues. Based on further processing of the pentasaccharide N-glycans are divided into three main classes: (i) high-mannose (ii) complex (iii) hybrid types.

High-mannose N-glycans have only unsubstituted mannose residues (typically 5-9) attached to the chitobiose core. Hybrid N-glycans contain both unsubstituted terminal mannose residues and mannose residues with a GlcNAc, which initiate "antennae" to which additional monosaccharides may be added. Complex N-glycans have GlcNAc residues added at both $\alpha$3 and $\alpha$6 mannose sites, do not have extra-pentasaccharide mannose residues and are found in bi, tri and tetraantennary forms.

Proteoglycans have one or more glycosaminoglycan (GAG) chains attached through a core region ending with a xylose to the hydroxyl groups of a serine residue. The most important glycolipids are glycosphingolipids, which consist of a glycan usually linked via a glucose or galactose to the terminal hydroxyl group of a ceramide lipid moiety, which is composed of the long chain amino alcohol sphingosine and a fatty acid.

Glycan Binding Proteins

Many of the specific biological roles of glycans are mediated via recognition by glycan binding proteins (GBPs). GBPs include lectins, glycosaminoglycan binding proteins and glycan-specific antibodies. Lectins often bind to terminal regions of glycan chains through carbohydrate recognition domains. Due to low affinity binding, multivalent CRD-glycan interactions are often required for interactions with biological relevance.

Glycan Processing

Glycans are primarily synthesised by glycosyltransferase enzymes which assemble monosaccharide moieties into glycan chains. Glycosyltransferase enzymes have in common the property of being able to catalyze transfer of a monosaccharide of a simple nucleotide sugar donor (for example, UDP-Gal, GDP-Fuc or CMP-Sia) to an acceptor substrate.

Glycoconjugate biosynthesis is initiated by glycosyltransferase enzymes which attach saccharides to a polypeptide side chain or sphingolipid base. For example, in the case of N-glycans, oligosaccharyltransferase transfers the glycan $Glc_3Man_9GlcNAc_2$ to the side chain of asparagine.

The majority of glycosyltransferases elongate glycan chains. Linear or branched chains are built by sequential glycosylation, often by distinct glycosyltransferases. That is, the product of glycosylation by one enzyme produces the preferred substrate for another. Examples of glycosyltransferases include galactose-1-phosphate uridyltransferase (GalT), N-acetylgalatosaminyltransferase (GalNAcT), fucosyl transferase (FuT) and sialyltransferase (SialT, which catalyze the addition of galactose, N-acetylglucosamine, fucose and sialic acid residues, respectively.

Glycosidases are glycan processing enzymes which remove monosaccharide moieties to form intermediates which are then acted upon by glycosyltransferases. This type of processing is particularly important in the biosynthesis of N-glycans; action of glycosidase enzymes on the $Glc_3Man_9GlcNAc_2$ allows formation of intermediates necessary for processing ultimately to high-mannose, complex and hybrid type N-glycans described above.

Microarrays

There is an increasing tendency in molecular biology towards miniaturization of assays, e.g. making use of binding agents immobilized in small, discrete locations as arrays on solid supports or on diagnostic chips. The use of microarrays can be particularly valuable as they can provide great sensitivity and require only very small amounts of biological sample from individuals being tested and allow a variety of separate assays can be carried out simultaneously, allowing high-throughput analysis.

Microarrays are libraries of biological or chemical entities immobilised in a grid/array on a solid surface and methods for making and using microarrays are well known in the art. The entities immobilised in the array can be referred to as probes. These probes interact with targets (DNA, RNA, protein, etc.) and the nature, extent and/or result of interactions can thereafter be assessed using fluorescent, enzymatic, stable isotope, radioisotope, mass, small molecule or immunogenic labels or label-free methods (e.g. scanning Kelvin microscopy, mass spectrometry, surface plasmon resonance, etc.). Interactions may include binding, hybridization, absorption, adsorption or probe or target processing such as enzymatic modification.

Glycan Microarrays

Microarrays using multi-well plate or printed slide formats have been developed to array glycans, allowing high-throughput screening against protein, nucleic acid and pathogen binding partners. Glycan microarrays use chemistry developed by Feizi and colleagues in the 1980s, in which lipid linkers are attached to the reducing end of native glycans, creating "neoglycolipids" and allowing analysis of the specificity of glycan binding protein by immobilization on a surface. In recent years, glycan libraries, efficient glycan immobilization strategies and applications for analysis of glycan binding protein specificity have been developed.

Binding Agents

The examples below provide uses of the present invention in the context of N-glycans as binding agents. However, the present invention encompasses the use of any other type of molecule as a binding agent. By way of example and without limitation, binding partners include microorganisms or associated molecules, carbohydrates, proteins, (including antibodies), peptides, lipids, nucleic acids (and analogs), large and small organic and inorganic molecules, drugs; and fragments, derivatives, metabolites, conjugates or hybrids of any of the above. The skilled person is well able to identify other types of molecule useful as a binding agent in the microarray of the invention and the techniques disclosed herein for preparing microarrays are adaptable for these different types of array.

Solid Substrates

A variety of solid substrates may be used in microarrays. Physical and chemical properties of the microarray chip surface influences microarray performance by determining specific and non-specific binding of target and non-target proteins. This in turn effects binding agent density on the chip surface and thus sensitivity of the microarray, distance between immobilized binding agents and the chip surface and their orientation, and thus access to interacting partners.

The choice of solid substrate also has implications for array applications. Opaque gold and aluminium oxide-coated surfaces are often used because their electrical conductivity and easy functionalization makes them suitable for use in a variety of applications with electrochemical read-outs. By contrast, silicon or glass substrates are preferred for applications with optical readouts due to transparency (for glass) and low intrinsic fluorescence. However, silicon-based array surfaces are often not uniform, and glass slides are not suitable for direct analysis by mass spectrometry.

The present invention encompasses all solid substrates suitable for use in surface and microarray assays. In the examples given below, Indium Tin Oxide (ITO)-coated glass slides are used a solid substrate. ITO slides are both electrically conductive and optically transparent, and are thus suitable for use in a wide variety of applications with both electrochemical and optical read-outs. Accordingly, the present invention encompasses any other substrate having properties making it suitable for use in multimodal analyses, such as glass slides coated with a transparent conducting oxide (TCO). Examples of TCOs include, by way of example but not limitation, aluminium zinc oxide (AZO), fluorine doped tin oxide (FTO) and indium doped cadmium oxide.

In other embodiments, the present invention may use solid substrates comprising transparent conducting polymers, including—but not limited to—polyacetylene, polyaniline, polypyrrole, polythiophenes and any polymer having conjugated double bonds (thereby allowing electrical conduction) and a band gap large enough to make it transparent to light. Specific examples include poly(3,4-ethylenedioxythiophene) (PEDOT), poly(styrene sulfonate) (PSS)-doped PEDOT and iodine- or 2,3-dichloro-5,6-dicyano-1,4-benzoquinone (DW)-doped Poly(4,4-dioctylcyclopentadithiophene). Carbon nanotubes are also suitable for use in the solid substrate of the invention, having the properties of high electrical conductivity and transparency.

Similarly, slides may be coated with transparent layers of metal, such as gold, the layers being less than 20 nm, preferably 5-10 nm thick.

Surface Chemistries

The microarray surface provides the environment for array assays. Ideally, it will provide an environment that optimizes the activities of immobilized molecules and minimize non-specific interactions. Broadly, surface chemistries used for microarray chips include polymeric materials, hydrogels and self-assembled monolayers (SAMs).

Polymeric surfaces are often non-homogeneous and are prone to non-specific interactions. Hydrogels are composed of lightly cross-linked polymers (for example polyacrylamide, dextran and agarose) which swell in water to provide a three-dimensional environment approximating to that in solution. They are relatively effective at preventing non-specific adsorption and facilitate higher loading capacity of immobilized species, but mass transport can influence interactions in assays.

Self-Assembled Monolayers

SAMs allow stringent control over surface structure and provide a homogenous environment around immobilized molecules. These surfaces are prepared by the spontaneous self-assembly of small organic precursor molecules—typically long-chain alkanethiols or alkylsilanes—by adsorption onto a solid substrate. These molecules have at least one functional group for adsorption to the solid substrate. Typically, precursor molecules used for the formation of SAMs also have a second, terminal functional group, for covalent or non-covalent binding agent immobilization.

In the examples provided below, the SAM is formed by covalent attachment of NHS-activated stearic acid to a silanized surface. With respect to the SAM, the present invention encompasses any molecule having properties making it suitable for generating a SAM. Particularly, the present invention may use any SAM consisting of a hydrophobic molecule, suitable for the formation of hydrophobic interactions with the chosen linker molecule (see below). These include, without limitation, functionalized fatty acids or any other functionalized hydrophobic molecule having a hydrocarbon chain. Preferably, the hydrocarbon chain is a saturated alkyl chain, such as found on a C10 to C36 fatty acid.

For the purposes of the present invention, the solid surface and SAM constituent may be functionalized by any means suitable for their stable association. These include, but are not limited to, the covalent and non-covalent methods of attachment described herein.

Immobilization

The chemical and structural diversity of glycans is problematic for their unbiased, reliable and reproducible immobilization on microarrays. Broadly, immobilization methods employed in microarrays can be divided into covalent and non-covalent strategies.

Whilst the covalent and non-covalent immobilization methods described below refer to immobilization of a binding agent to a surface, the present disclosure encompasses use of any of these chemistries/strategies—in either orientation—for the attachment of (i) any SAM-forming molecule to a solid substrate; (ii) any linker molecule to any SAM; (iii) any linker molecule to any binding agent; and (iv) any SAM-forming molecule to any binding agent.

Covalent Immobilization

Covalent immobilization allows specific attachment via known functional groups. Thiol and amine chemistries are the most commonly used means of covalent immobilization.

Binding agents having or functionalized with thiol groups may be immobilized on surfaces presenting maleimide, aryl- or carbon-carbon double-bond-containing groups through formation of stable carbon-sulfur bonds, or through interactions with aziridine-functionalized surfaces. Disulfide exchange reactions with thiol-functionalized surfaces may also be used.

Amine chemistry is the most widely used immobilization strategy. Amine-terminated binding agents may be immobilized using (i) amine/cyanuric chloride coupling (as in commercially-available Glycominds chips); (ii) amide bonding through reactions with N-hydroxysuccinimide (NHS)-ester-, carboxcylic acid-, carbonate-, anhydride- or acyl group-functionalized surfaces; (iii) amidine formation through reaction with imidoester-functionalized surfaces; (iv) sulphonamide formation through reactions with sulfonyl halide-functionalized surfaces; (v) aniline formation through reactions with surface presenting aryl groups; (vi) imine formation through reactions with aldehyde-functionalized surfaces; (vii) amino ketone formation through Mannich reactions with aldehyde-functionalized surfaces; (viii) guanidiune formation through reactions with carbodiimide-functionalized surfaces; (ix) urea formation through reactions with isocyanate-functionalized surfaces; (x) thiourea formation through reactions with isothiocyante-functionalized surfaces, or; (xi) aminoalcohol formation through reactions with epoxide-functionalized surfaces.

Hydrazide- or oxyamine-terminated binding agents may be immobilized in the same way.

Carboxylic acid-functionalised surfaces may also be used to immobilize functionalized with carbodiimide and diazoalkane groups, whilst surfaces presenting hydroxyl groups may be used to immobilize isocyanate- and epoxide-functionalized binding agents.

Functionalized binding agents may also be immobilized through cycloaddition reactions between functional groups having a conjugated diene and groups having a substituted alkene through Diels-Alder chemistry, or using "click" chemistry, through reactions between nitrile and azine groups.

In any of the above described covalent couplings, the binding agent-surface orientation of functional groups may be reversed.

An alternative means of covalent attachment not requiring prior binding agent derivatization utilizes array surfaces having photoreactive groups such as benzophenone, diazo, diazirine, phthalamido and arylazide groups.

Covalent attachment to microarray surfaces typically requires high binding agent concentrations that are not suitable when working with complex glycans or glycans/binding agents present in complex samples.

Non-Covalent Immobilization

Binding agent immobilization may be achieved by adsorption through non-covalent hydrophobic, hydrophilic or electrostatic interactions, which will depend on the binding agent and surface involved. Binding agents will adsorb to polymeric materials such as, for example, nitrocellulose, polystyrene, polypropylene, polycarbonate and poly(ethylenimine).

Non-covalent immobilization may involve electrostatic interactions between binding agents and surfaces modified to contain positively- or negatively-charged groups, such as amine or carboxy groups, respectively.

Binding agents having or functionalized with thiol groups may be immobilized on gold surfaces through semi-covalent interactions between gold and sulphur groups.

However, binding agents are orientated at random in such arrays, giving low sensitivity, and efficient immobilization requires binding agents to have a large molecular weight; immobilization of lower molecular weight binding agents has typically been achieved by modification with long-chain alkyl linkers.

Alternatively, binding agents may be non-covalently immobilized in a defined orientation using fluorophilic, biotin-streptavidin, histidine-Ni or -Co and complementary ss-DNA interactions between tagged binding agents and binding partner-coated surfaces, in either orientation. These methods are, however, difficult, uncertain and employ multiple and expensive tagging steps.

In addition to those described above, other covalent and non-covalent means of attachment may be employed in microarrays and are well known to those skilled in the art.

Hydrophobic Linker Molecules

Microarrays have been developed in which binding agents are functionalized with a hydrophobic linker and non-covalently immobilized by insertion into a SAM through hydrophobic interactions.

Immobilization in this way allows arrays to be formed with binding agents at low concentrations, without the need for multistep tagging, whilst retaining appropriate binding agent orientations and associations stable enough for repeated washing and incubation steps.

As demonstrated by the examples provided below, the present invention may use bidentate lipophilic linkers, with two, unbranched long-chain alkyl tails. These maximise the potential for hydrophobic interactions, and thereby strengthen association with the NHS-stearic acid SAM.

With regard to linker molecules, the present invention encompasses any molecule having the essential property of being suitable for non-covalent immobilization in a SAM through hydrophobic interactions. These include, by way of example, any molecule having a hydrocarbon chain. Preferably, the hydrocarbon chain is a saturated alkyl chain. Hydrophobic linker molecules may be mono- bi- or polydentate. Generally, the linker will have a $C_{6-20}$ hydrocarbon chain, more preferably a $C_{8-16}$ hydrocarbon chain, and most preferably a $C_{10-14}$ hydrocarbon chain.

With regard to linker functionalization for binding agent immobilization, linker molecules may be functionalized by any means suitable for stable immobilization of the binding agent of interest. These include, but are not limited to, the covalent and non-covalent methods of attachment described herein.

In the examples provided below, compound 2 uses a polyethylene glycol (PEG) spacer. Accordingly, the present invention encompasses linker molecules having a spacer between hydrophobic region for non-covalent association in the SAM and the functional group for binding agent immobilization. Such spacers may facilitate certain associations with the immobilised binding agent that may otherwise have been sterically inhibited. Appropriate spacer regions can be easily identified by the skilled person and incorporated into linker molecules by simple chemical modifications well known in the art. Examples include polyethylene glycol polymers, such as hexaethylene glycol (HEG) and PEG100.

The Microarray Surface

In the examples below, the ITO surface presents hydroxyl groups, which are silanized with 3-aminopropyltriethoxysilane (APTES) to give an amino-functionalized surface. Alternatively, a one step silanisation reaction my be used, for example using a direct silanisation reaction with octadecyltrichlorosilane (OTS) that is capable of producing substrates with a similar hydrophobicity to that produced by the two-step process with APTES. Other silanisation reagents that may be used in accordance with the present invention include the use of tetraethyl orthosilicate (TEOS) and Piranha solution.

A SAM is subsequently created by covalent coupling of NHS-activated stearic acid.

In contrast to previously-described methods, bidentate, hydrophobic linker molecules functionalized with terminal NHS-ester groups are inserted into the SAM. This results in the generation of a surface primed for the immobilization of amine-terminated species, where immobilization is achieved through hydrophobic interactions through the tails of bidentate lipid linker molecules.

The advantageous properties of both covalent and non-covalent coupling strategies are thus combined, to give a uniform and resilient microarray surface with unparalleled flexibility. As the binding agent to be immobilized does not require labelling, the present invention is particularly suitable for low-cost, high-throughput analyses.

Detachment for Analysis by MALDI-Tof

The method of binding agent immobilization has implications for downstream analyses. Analysis by MALDI-Tof mass spectrometry requires detachment of immobilized binding agents from the microarray surface.

Covalent immobilization methods suitable for such downstream analyses include immobilization with photocleavable linkages, and the use of surfaces employing SAMs that desorb from the microarray surface under laser irradiation. Binding agents immobilized through non-covalent fluorous and hydrophobic interactions also allow direct analysis by MALDI-Tof.

In the examples described below, detachment for MALDI-Tof is achieved by laser-assisted desorption, through disruption of hydrophobic interactions of linker portions of covalent binding agent-linker conjugates from the NHS-steric acid SAM.

Glycan Microarray Assays

Glycan microarrays may be used to identify and characterize glycan-binding partner interactions (both qualitatively and quantitatively), using labelled species, surface plasmon resonance (SPR)- and mass spectrometry-based technologies. Mass-spectrometry has also been used to analyze glycan processing, through on-chip analysis of reaction products following enzymatic modification.

Glycan-binding partner interactions may be identified and characterised by direct detection using fluorescent, enzyme, stable isotope, radioisotope, mass, small molecule, affinity or immunogenic label-tagged glycans/putative binding partners, or by indirect detection using antibodies. SPR analysis has allowed the quantitative determination of affinities of such interactions. Mass-spectrometry-based techniques allow the label-free identification of binding partners, as well as the characterization of activities, substrate specificities and efficiencies of glycan-processing enzymes.

As described above, the final microarray surface integrates the choice of solid substrate, surface chemistry and immobilization strategy, and has implications for the interactions that can be studied and the types of analysis that can be performed. For example, an opaque substrate such as gold is not suitable for transmission optical readouts, whilst substrates non-conductive substrates like glass and aluminium oxide are not suitable for analysis by MALDI-Tof MS. Similarly, certain surface chemistries and/or methods of immobilization are not suitable for studying certain types of glycan interactions; they may, for example, bias the type of glycan immobilized, or sterically restrict access of a given interacting partner.

In the examples provided below, the inventors perform assays with optical readouts and mass-spectrometry based analyses. The present invention is also compatible with analytical techniques that may be used with other surface and/or microarrays. By way of example, and without limitation, these include techniques using fluorescent, enzymatic, stable isotope, radioisotope, mass, small molecule, affinity or immunogenic labels and label-free methods such as scanning Kelvin microscopy and SPR.

Due to the conductive and transparent properties of ITO-covered glass slides, the above methods may be performed on the same samples in the same arrays. Such multimodal analyses improve assay resolution and allow more robust conclusions to be drawn. Moreover, the capacity for multimodal analyses using the present invention allows initial scanning using low resolution methods and subsequent follow-up in-depth analysis. In this way, time, reagents and resources are used more efficiently. For example, initial screening by fluorescence analysis of binding of a fluorescently-labelled binding partner to an immobilized binding agent can be determined, and then mass-spectrometric analysis of binding agent processing can be determined only in those wells in which binding has taken place.

Applications

Whilst the examples provided below relate to glycan microarrays, the surfaces and methodologies described herein are clearly useful in all types of microarray and/or surface-based analyses.

By way of example and without limitation, the same or similar surfaces can be used for the investigation of microorganisms and associated molecules, proteins, (including antibodies), peptides, lipids, nucleic acids (and analogs), large and small organic and inorganic molecules, drugs; and fragments, derivatives, metabolites, conjugates or hybrids of any of the above.

Accordingly, the present invention may use any of these classes of substances as binding agents for making microarrays of the present invention. Equally, any one of the above may be a component of a test sample which is applied to a microarray of the invention. Any possible binding agent-test sample component combination of the above may be used in the context of the present invention.

The microarray of the invention may be used to perform or analyse any possible process involving a binding agent and a test sample component. Such processes include binding and modification.

Binding may be through hybridization, absorption and adsorption, and may occur through covalent or non-covalent interactions between the binding partner and test sample component.

Accordingly, the microarray of the invention is useful in determining if a binding agent is capable of binding a component of a test sample, and vice versa. Subsequent analyses of interacting binding partners and test sample components may be used for the identification of previously unknown interactions. Analyses may be used to investigate the nature of an interaction, including relative and quantitative determination of extent or strength of an interaction, the determinants of an interaction such as residues involved in binding on a binding agent or test sample component.

Interactions may be identified by detecting the presence, amount or activity of a label such as a fluorescent, enzymatic, stable isotope, radioisotope, mass, small molecule, affinity or immunogenic label on one or more binding partner and/or test sample component, or through label-free methods such as mass spectrometric analysis, scanning Kelvin microscopy and surface plasmon resonance (SPR). In some embodiments, wherein the components of the test sample are labelled prior to applying the sample to the array. However, in some cases this pre-labelling may lead to high background signals on detection. Generally, and especially when background signal is high, it is preferred that the components of the test sample are labelled after binding to one of the binding agents in the microarray.

The microarray of the invention is also useful for determining the identity of one or more interacting species through downstream analysis using, for example, mass-spectrometry based technologies such as MALDI-Tof.

Moreover, for complex molecules, the configuration of constituent parts can be determined. An example of a complex molecule is a biological polymer, such as a nucleic acid, protein, glycan or the like. MALDI-Tof analysis of one or more interacting species may be used to determine, for example, the sequence of a DNA, RNA, amino acid or carbohydrate molecule.

The microarray of the invention may be used to perform or analyse modifications to binding partners or test sample components. Modifications include, but are not limited to, any mass-, structure-, or chemistry-changing modification, including chemical and enzymatic processing.

Subsequent analyses of binding partners or test sample components may be used to determine modifications. These analyses are capable of characterizing the mass, structure or chemistry of a binding partner and/or test sample component. For example, mass spectrometry based technologies may be used to determine modifications.

The present invention is suitable for high-throughput bioassays for use in pharmaceutical and biomedical research. Without limitation, the present invention is useful for the following applications:

Biomolecular libraries—biomolecular libraries may be generated by the immobilization of precursor molecules on an array and in situ, followed by targeted (i.e. microarray spot-specific) enzymatic or chemical modification. Such libraries are useful in a wide variety of applications, including, but not limited to, drug screening, antibody development, etc.

Target identification—through mass-spectrometric analysis and subsequent profiling of partners bound to an immobilized entity, specific drug, pathogen or biomolecule targets can be identified.

Enzyme/chemical function screening—specific enzyme or chemical functions can be assayed in complex biological matrices. Arrays of substrates for specific enzymatic/chemical activities can be prepared and incubated with any potential enzyme/chemical source, for example biological samples such as cell extracts, or preparations of enzymes/chemicals of unknown function. Mass spectrometric analysis of substrate processing can then be used to identify and quantify enzymatic/chemical activities in the sample. This approach is particularly useful in the search for enzymes with desired activities and specificities in the bioprospection of microbial communities. For example, enzymes specific for particular glycosidic bonds are useful in biofuel processing, and proteases with certain activities or specificities are useful in food processing.

Inhibitor screening—inhibitors of any process that results in a change in mass of a substrate can be screened by mass spectrometry. Examples of such mass changing transformations are enzymatic reactions, and the method may therefore be used to identify enzyme inhibitors.

Biomolecule characterization/engineering—panels of variants of biomolecules involved in mass-changing transformations of an immobilized target substrate can be screened by mass spectrometry. In this way, variants maximizing a desired activity or minimizing an unwanted activity can be identified.

Chemoselective enrichment—arrays with lipid linker molecules functionalized with different groups can be used for the chemo-selective trapping of molecules with certain functional groups. Subsequent mass spectrometry and profiling can be used to assign identities to trapped species. Such an assay is thus used for the chemo-selective fractionation of complex mixtures by functional groups. For example, NHS-functionalized lipid linkers can be used to trap molecules having amine groups, whilst maleimide-functionalized linkers can be used to trap molecules having thiol groups. This approach can be used for enrichment from any potential source of a molecular subgroup of interest, including biological samples such as cell lysates, secretomes, microbiomes etc.

Biomolecule detection—as above, arrays with lipid linker molecules functionalized with groups for trapping of molecules with certain functional groups and subsequent mass spectrometry can be used for the detection of biomolecules in a sample. In this way, known biomolecules such as biomarkers for certain diseases/disease states or pathogen-related molecules can be detected. The present invention is therefore useful, for example, in diagnostics, prognostic monitoring and in the detection of contaminants such as toxins, drugs and pesticides in food or environmental samples.

Biomarker identification—Similarly, the present invention can be used to identify new biomarkers of a phenotype or infection by a pathogen by comparison of spectra of array-trapped species between different biological samples.

EXPERIMENTAL EXAMPLES

In the following experimental examples, the present invention is exemplified using "bottom up" attachment strategy involving non-covalent binding agent attachment to ITO-covered transparent glass slides to develop micrometer-scale microarrays. In situ attachment of glycans functionalized with a C5-aminolinker to a hydrophobic tag bound to slide surfaces allowed glycans to be attached on a picomolar scale, thus avoiding the wasteful off-chip binding agent tagging of other approaches.

Microarrays were then used for the multimodal analysis of glycan interactions, structures and modifications by MALDI-Tof-MS, fluorescence and optical microscopy. Specificities of various glycosyltransferases were assayed by incubation with selected lectins and by MALDI-Tof and MS/MS analysis. The examples provide a demonstration of the utility of the microarrays in the development of large glycan libraries by on-chip enzymatic processing. Furthermore, different glycoforms of a protein trapped on an array of lectins could be differentiated and analyzed and finally the inventors were able to trap, digest and identify a lectin bound to a glycan microarray by sequence homology.

Example 1

Preparation and Characterization of Hydrophobic ITO Slides

Surface Modification of ITO Slides

ITO covered slides were washed by immersion in basic piranha solution and silanized by shaking in 2% APTES (3-aminopropyl trietoxysilane) solution in $CH_2Cl_2$ for 2 h. Slides were then rinsed twice in $CH_2Cl_2$ solution, dried, cured at 80° C. for 2 h and purged with Ar. N-succinimidyl (NHS) stearic acid was synthesized by dissolving 600 mg stearic acid in 15 mL $CH_2Cl_2$ and mixing with 1.1 equivalents of N-hydroxysuccinimide (NHS) and Ar-(3-dimethylaminopropyl)-N'-ethylcarbodiimide hydrochloride (EDC) for 2 h at room temperature. After silanization, slides were coupled with NHS-activated stearic acid to create a hydrophobic SAM. Slides were treated with 10 mM NHS-stearic acid in DMF with 150 mM DIPEA overnight, washed, dried and purged with Ar. Slides were then stored at room temperature under vacuum until use.

Non-Silanized ITO Slides

Direct surface modification on non-silanized ITO slides was performed by overnight incubation with saturated solutions of tetradecanoic acid, stearic acid or oleic acid in $CH_2Cl_2$, or with 1-mercapto undecane.

Surface Characterization

Surface hydrophobicity and composition was analyzed by contact angle and XPS analysis. Analyses revealed complete functionalization of the ITO surface. Moreover, contact angle measurements demonstrated increased hydrophobicity for ITO slides functionalized with APTES and stearic acid than for those functionalized directly with stearic acid or an alkylthiolate (θ~85 compared with θ~40-70).

Synthesis of the Succinimidyl Carbonate-Type Hydrophobic Linker Compounds 1 and 2

The hydrophobic SAM was the support layer for the immobilization of lipid tagged biomolecules via hydrophobic interactions. To improve the strength of hydrophobic interactions, the present invention used the bidentate lipid linker 1,2-sn-dipalmitoyl glycerol. This lipid was either directly activated as a carbonate (compound 1) or further extended with a hexaethylene glycol spacer to improve biocompatibility and enzyme accessibility (compound 2).

Synthesis of Activated Bidentate Linker Compound 1

Figure 14:
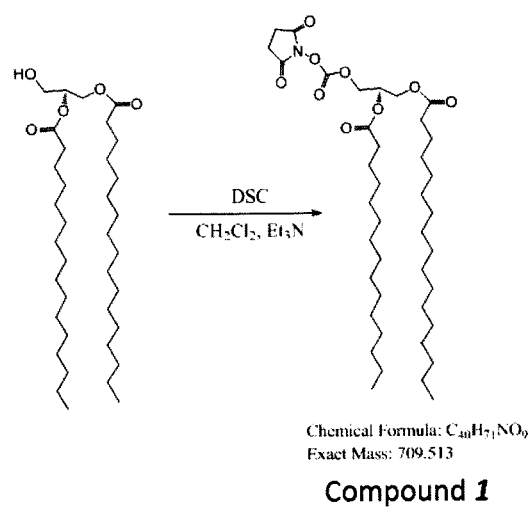
FIG. 14. Synthesis of activated bidentate linker compound 1.

100 mg (0.17 mmol) of 1,2-dipalmitoyl-sn-glycerol were mixed with 1.4 mmol of disuccinimidyl carbonate (DSC) and 3.4 mmol of trietylamine in 60 mL of dry $CH_2Cl_2$ at 0° C., and incubated at room temperature overnight (FIG. 14). The resulting compound (compound 1) was purified and confirmed by MALDI-Tof MS.

Synthesis of 1-aminohexaethylenglycol 3.5 mmol of $MeSO_2Cl$ were added to hexaethylenglycol solution (2.1 equivalents) and $Et_3N$ (1.3 equivalents) in 5 mL of THF at 0° C. and incubated at room temperature overnight. The solvent was removed, 1.5 equivalents of $NaN_3$ in 5 mL of EtOH were added and the mixture was refluxed overnight, cooled and the solvent removed. The crude was diluted in 15 mL of $Et_2O$, washed with 5 mL brine and 1-azidohexaethylenglycol was purified by flash chromatography (Hex:AcOEt gradient from 100% to 50%). The compound was hydrogenated by passing through H-Cube 10% Pd/C CatCart® cartridge, and checked by 1H-RMN and HRMS.

Synthesis of Activated Bidentate Linker Compound 2

Figure 15:
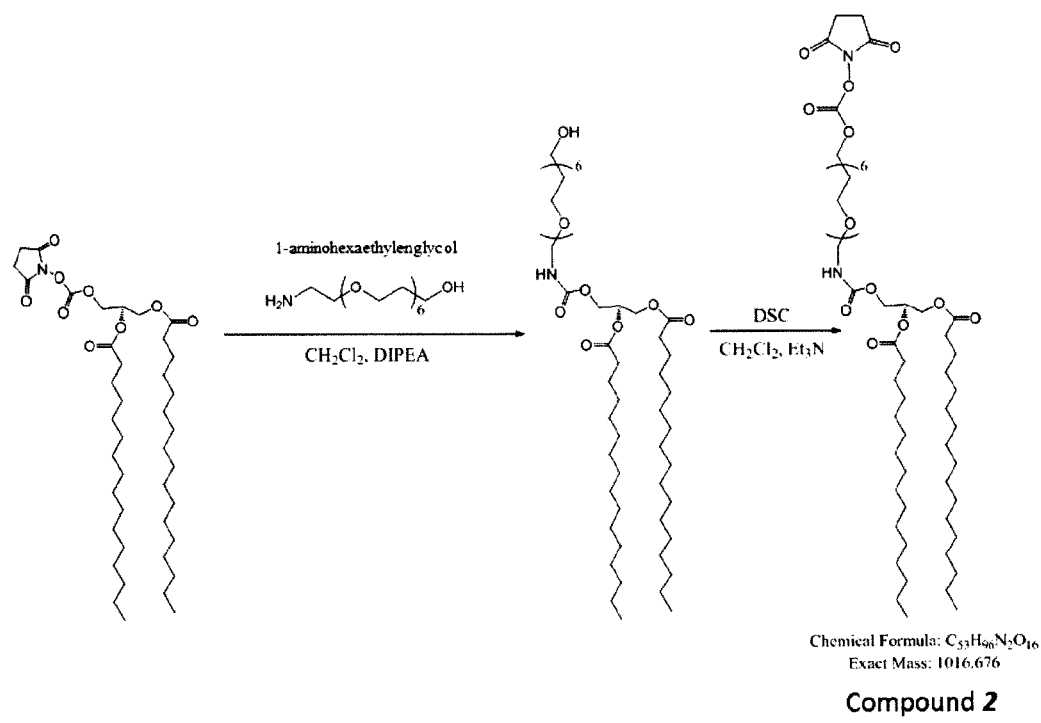
FIG. 15. Synthesis of activated bidentate linker compound 2.

35 mg of compound 1 (0.05 mmol) was mixed with 40 mg of 1-aminohexaethylenglycol (0.142 mmol, 2.8 eq.) in 15 mL of dry $CH_2Cl_2$ and 10 eq. of DIPEA, and incubated for 2 h at room temperature. The product was mixed with 4 equivalents of DSC and 1 mmol of TEA in 12 mL of dry $CH_2Cl_2$ at 0° C. and incubated overnight at room temperature (FIG. 15). The resulting compound (compound 2) was purified and confirmed by MALDI-MS.

Functionalization of the Hydrophobic ITO Slides

Compounds 1 and 2 were overlayed onto silanized ITO slides overlayed with N-succinimidyl stearic acid, to yield surfaces A and B, respectively (FIG. 1). The compounds were incubated with the slides in 1 mM chloroform at room temperature overnight, slides were then washed, dried and stored at −20° C. or at room temperature under vacuum. Surface functionalization was monitored by surface XPS analysis. Surfaces A and B represent novel, reactive surfaces suitable for the direct printing of binding agents, bypassing the need for binding agent pre-tagging as required in previously described methods.

Example 2

Printing and Characterization of Glycan Arrays

Robotic Printing of Glycans

Figure 2:
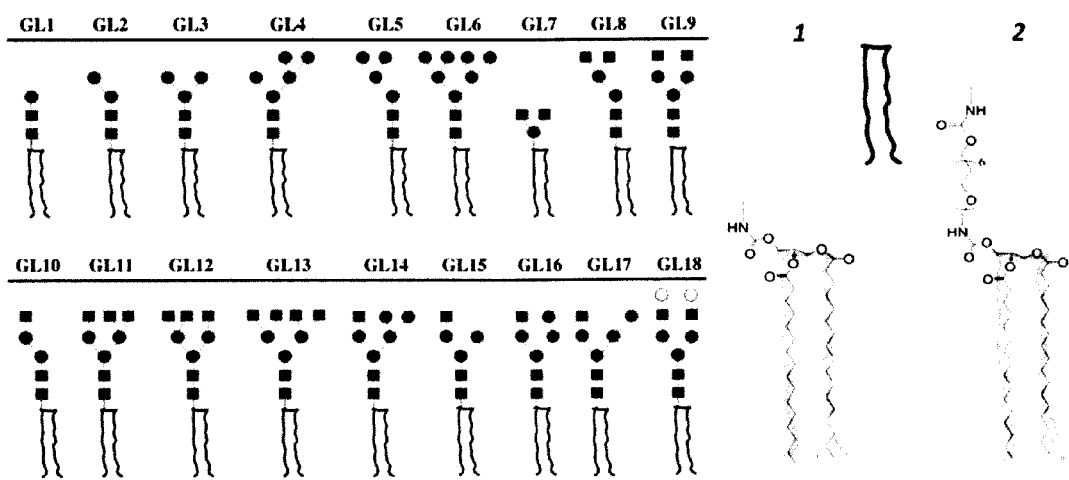
FIG. 2. Schematic representations of glycolipid compounds formed by reaction of C5-amino linked N-glycans G1-G18 with bidentate linker compounds 1 and 2.

Stock solutions of C5-amino linked N-glycans G1 to G18 were prepared at 50 μM in phosphate buffer (300 mM, pH 8.7). Aliquots of ~15 mL of each glycan (~0.7 pmol) were applied to slide surfaces with a dot pitch of 750 μm, and slides were incubated overnight at room temperature in a humidity chamber. Slides were subsequently washed by sonication in water and dried in a stream of Ar. FIG. 2 provides schematic representations of glycolipid compounds formed by reaction of C5-amino linked N-glycans G1-G18 with bidentate linker compounds 1 and 2 on surfaces A and B, respectively.

Characterization of the Glycan Array (i) Using Labelled Lectins

Arrays were quenched with 50 mM ethanolamine (in 50 mM borate buffer, pH 9.3) for 1 h, and passivated with 2% BSA in PBS for 1 h. Fluorescently-labelled lectins in PBS buffer containing 2 mM $CaCl_2$ and 2 mM $MgCl_2$ were used to detect immobilized glycans.

For array characterization, fluorescently tagged Wheat Germ Agglutinin (WGA), which binds strongly to chitobiose, a moiety present on each glycan of the arrays, was used. After 1 h of incubation, slides were washed in PBS and water, dried and scanned on a microarray scanner. Spot size and fluorescence intensity for each glycan was determined using ScanArray Express software.

Figure 3A:
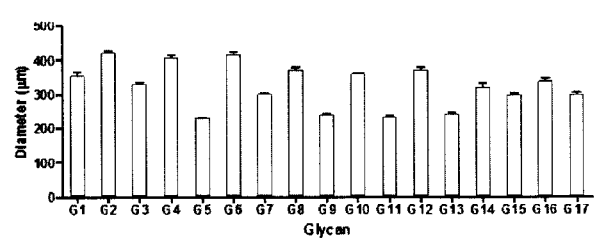
FIG. 3A-FIG. 3B. Spot diameters by array glycan and spotted amount. Glycans were spotted on arrays and detected with fluorescently-labelled WGA.
Figure 3B:
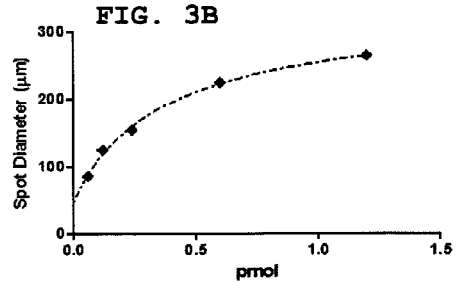

FIG. 3A shows that glycans spotted at 1.2 pmol formed homogenous spots with diameters between 220 and 450 μm, and with low spot-to spot variance of 2-7% depending on glycan type. FIG. 3B demonstrates that spot diameter reaches saturation at a spotted amount of ~1.2 pmol.

Figure 4A:
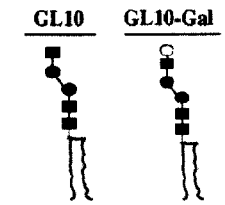
FIG. 4A-FIG. 4B. Detection limits for glycan-lectin pairs.
Figure 4A:
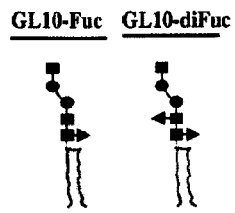
Figure 4B:
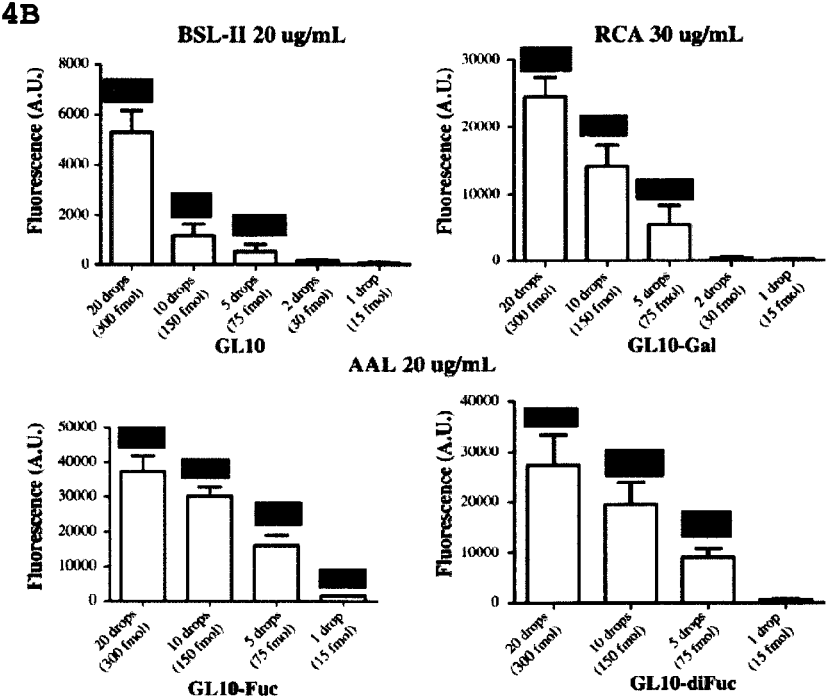

Detection limits for glycan-lectin pairs were determined using standard concentrations of labelled lectins (*Aleuria aurantia*, AAL, 20 μg/mL; *Ricinus communis* Agglutinin, RCA, 30 μg/mL and *Griffonia* (Bandeiraea) *simplicifolia*, BSL-II, 20 μg/mL) and decreasing quantities (from 300 to 15 fmol) of four different C5-aminoglycans (FIG. 4A). FIG. 4B bottom right panel shows as little as 15 fmol of bifucosylated compound GL10-diFuc was detectable with fluorescently-labelled fucose-binding lectin AAL.

Figure 5:
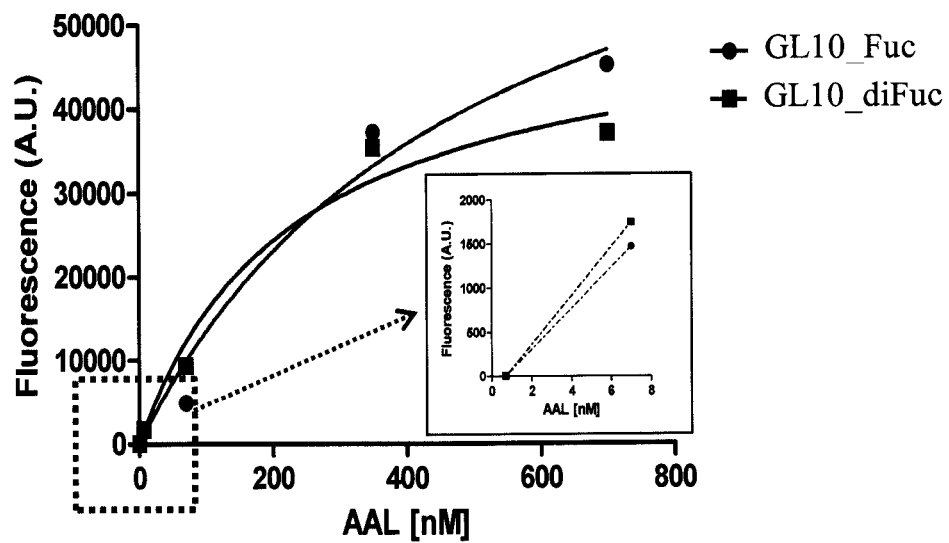
FIG. 5. Fluorescence signal from glycans spotted at 0.7 pmol/spot detected with fluorescently-labelled AAL at the indicated concentrations.

FIG. 5 shows that glycans GL10_Fuc and GL10_diFuc spotted at 0.7 pmol/spot gave strong fluorescence signal (>15000 A.U.) following detection with as little as 7 nM of labelled AAL. A glycan spotting concentration of 0.7 pmol/spot was therefore used in subsequent arrays.

Thus, the present invention demonstrates that direct printing of aminopentylglycosides onto surface A and B slides produced arrays with homogenous spot morphology, avoiding solubility problems and strict incubation requirements associated with printing lipid or fluorescently-tagged glycans. Arrays constructed in this way have the further advantage that linker type and length can be adjusted and the surface optimized according to specific experimental requirements. Again, these properties represent a significant advantage over other approaches which require pre-tagging of binding agents.

(ii) MALDI-Tof Analysis

Glycan arrays were over-spotted using 4 mg/mL matrix solution (2,5-dihydroxibenzoic acid, DHB, in water:acetonitrile, 90:10, and 0.002% of sodium formate). Slides were dried and analyzed by MALDI-Tof using an Ultraflextreme III mass spectrometer. Acquisitions (2000-3000) were carried out in positive reflector ion mode with a pulse duration of 50 ns, laser fluence of 40% and laser frequency of 500 Hz. Laser intensity was set marginally above the threshold of ionization to avoid fragmentation and the m/z range was chosen according to the mass of the sample. All peaks were detected as sodium adducts with high intensity signal (>1000 U.A.) and low in-source fragmentation (less than 5% for all the cases).

Glycans on Surface A or B

Figure 6:
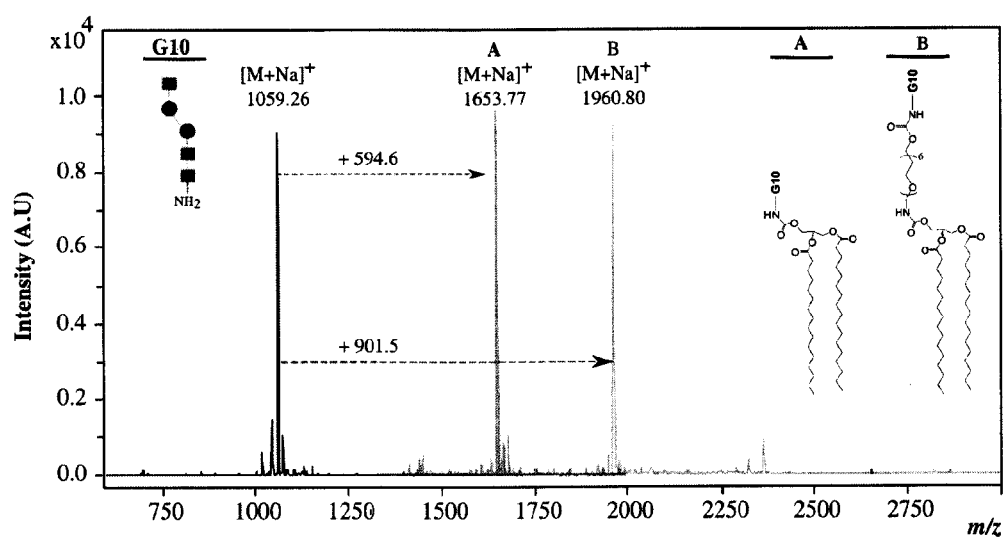
FIG. 6. MALDI-Tof MS overlay of free G10 glycan (m/z 1059), after its immobilization on surface A (m/z 1653) and on surface B (m/z 1960).

For each glycan, three different species could be detected; (i) free, unbound glycan, (ii) the glycolipid formed by reaction of the glycan with compound 1 on surface A, and (iii) the glycolipid formed by reaction of the glycan with compound 2 on surface B. FIG. 6 provides a combined spectrum for exemplary aminoglycan G10. The peak, at m/z 1059.26 corresponds to free G10. When G10 is bound to surface A, an increase in mass of +594.6 is observed as a result of the introduction of the bidentate hydrophobic tail of compound 1 (FIG. 6). Similarly, when G10 is bound to surface B an increase in mass of +901.5 is observed due to the reaction with compound 2 (FIG. 6). MALDI-Tof analyses of arrays revealed efficient removal of unreacted glycans and buffer constituents, leaving only the immobilized, newly formed neoglycolipids on surfaces A and B.

(iii) MALDI-Imaging of Glycan Array

For MALDI-imaging, 54 spot arrays were analyzed within 90 min of printing DHB matrix. Analyses were performed using an UltrafleXtreme III MALDI-Tof/Tof and images were acquired using FlexControl 1.3 software (Bruker Daltonics). Five hundred shots in positive ion mode were collected per pixel in random walk mode (laser frequency 1 kHz), at an accelerating voltage of 25 kV, a grid voltage of 22.3 kV and a delay time of 90 ns. Baseline subtraction and normalization was performed using the Bruker software FlexImaging 2.1.

A resolution of 75×75 µm gave 36 points or spectra per spot in a scan of 1.30 h (18 points/min). Very high intensity signals were detected as sodium adducts by MSI with high S/N ratios (S/N >100 for standard experiments), and the complete absence of cross-contamination of adjacent spots during printing and matrix spotting was confirmed. The spotwise analysis of the 54-spot array was completed in less than 3 minutes.

Surface Validation

Following validation of miniaturization of the dual optical and MALDI-Tof readout glycan array, the present invention was used to investigate array sensitivity, stability and reproducibility.

(i) Detection Limit

Figure 7:
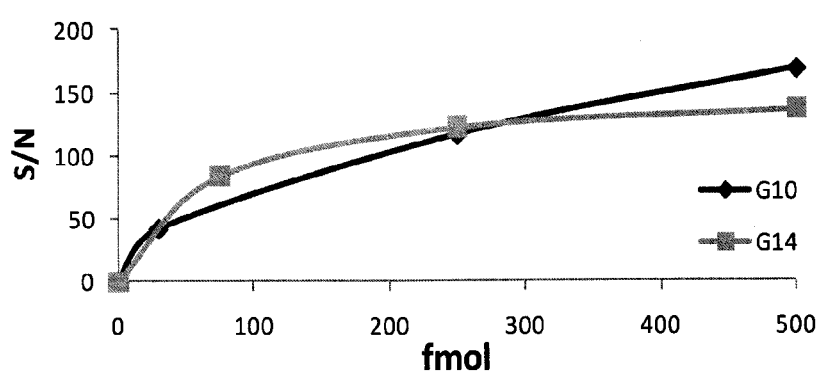
FIG. 7. Glycan detection by MALDI-imaging.

Different quantities (5 replicates, 0 to 500 fmol) of glycans G10 and G14 were spotted onto surface A, incubated overnight, washed and matrix spotted. FIG. 7 shows that the detection limit was calculated to be ~30 fmol (giving a S/N ratio of 40 for glycan G10). This represents the most sensitive method available for the analysis of immobilised binding agents, such as glycans, by mass spectrometry.

(ii) Stability Against Washings

Figure 8:
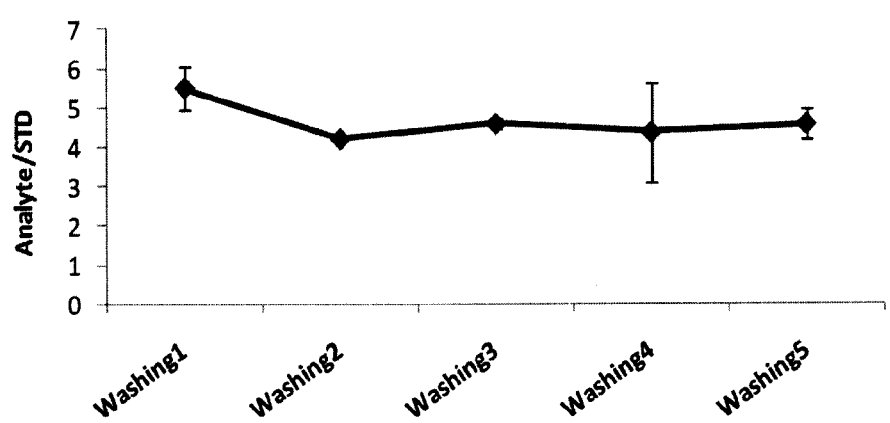
FIG. 8. Stability of non-covalent association of GL11 with surface A to repeated 5 min wash steps with sonication.

Stability of hydrophobic interactions against successive aqueous washings was analyzed. 0.5 µL of 50 µM G16 glycan was manually applied to surface A slides, incubated overnight in a humidity chamber, subjected to a first 5 minute wash step and dried. Slides were then subjected to 5 steps of washing with sonication (5 min each), dried and MALDI-Tof MS spectra were recorded. 0.5 µL of GL11 glycolipid (~0.04 pmol; synthesized by reacting G11 glycan with compound 1) were added to DHB matrix mixture for use as an internal standard. FIG. 8 shows the high stability of non-covalent associations of GL11 with surface A to repeated washing steps; the analyte to standard ratio barely changed across the 5 washing steps. This extraordinary stability makes the arrays of the invention suitable even for extended and multistep enzymatic on-chip glycan modifications without loss of immobilized glycans during washing steps.

(iii) Use of Detergents

Surface stability was analyzed with Triton X-100 and Tween20. Immobilized glycans were incubated with 0.001 to 0.5% dilutions of detergent and checked by MALDI-Tof for analyte removal. Results showed compatibility for the use of Triton X-100 and Tween20 up to 0.01%; higher amounts caused removal of a variety of printed analytes.

(iv) Reproducibility

Figure 9:
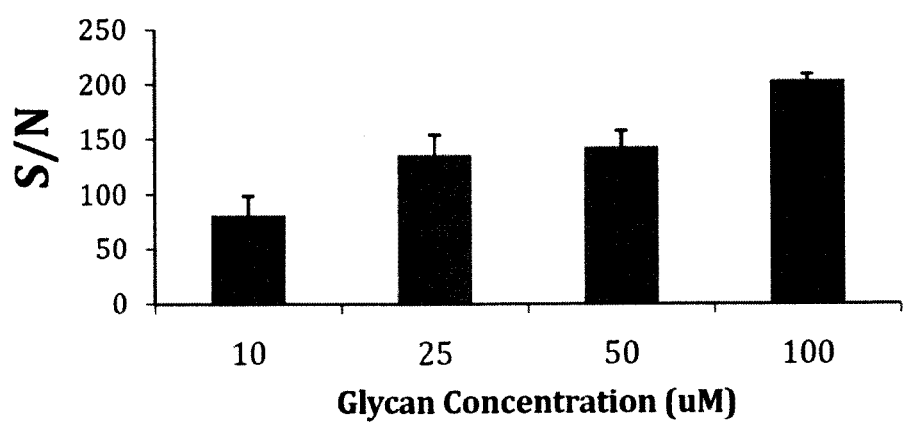
FIG. 9. Slide-to-slide reproducibility of glycan detection by MALDI-MS.

Different concentrations of N-glycans (10, 25, 50 and 100 µM) were spotted in different wells on 4 different slides prepared at the same time and analyzed by MALDI-MS. Good reproducibility of S/N values was observed for a range of glycan concentrations on different slides, and reproducibility was found to increase with spotting concentration (FIG. 9). Glycans spotted at 100 µM showed very low S/N ratio variation (1-13%).

Example 3

On-Surface Enzymatic Screening

Biocompatibility

Figure 10:
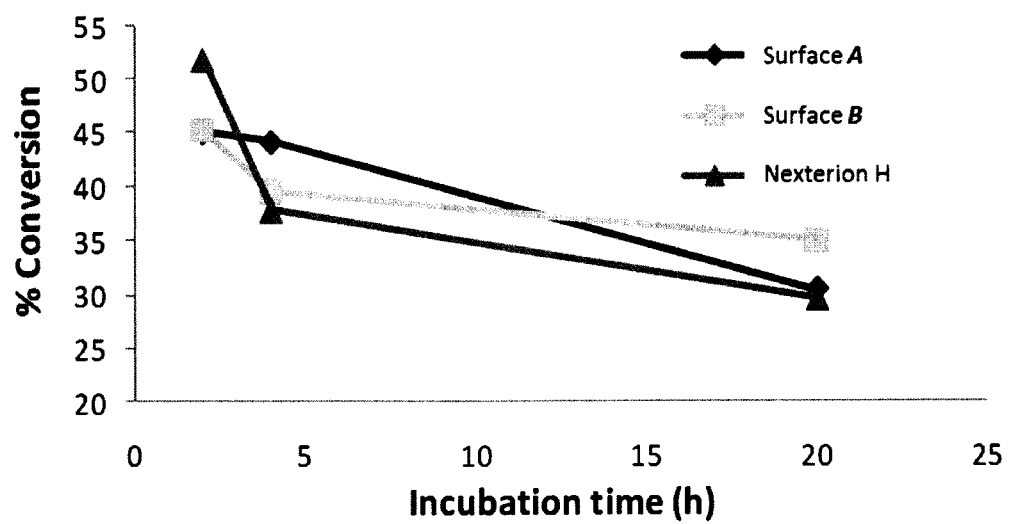
FIG. 10. Biocompatability of Surface A, Surface B and Nexterion® H slides. Activity of GalT as measured after 2, 4 and 20 h incubation on the different slides.

Surface biocompatibility was confirmed using GalT (β-1, 4-galactosyltranferase) and by comparison to commercial, hydrogel surface-based Nexterion® H slides. Surface A, B and Nexterion H slides were passivated with 2% BSA solution for 20 min and incubated with GalT for 2 h, 4 h or overnight at 37° C. The enzyme cocktail was subsequently transferred to a pNPGlucNAc containing solution and lost activity was determined by analysis of relative pNPGlucNAc and reaction product pNPLacNAc levels by UPLC. FIG. 10 shows that GalT retained high enzymatic activity following 2, 4 and 20 h incubation on each surface. Surfaces A and B both preserved activity better than Nexterion® H following 4 and 20 h incubations. Surface A was found to retain highest activity following 4 h incubation, whilst surface B retained highest enzyme activity following prolonged incubation (20 h).

Detection Limit by MALDI-Tof of the Converted Compound

G10 glycan was galactosylated in solution to form G10_Gal, which was subsequently confirmed by MALDI-MS and purified. Different concentrations of G10 were mixed with G10_Gal (from 0 to 17% of G10_Gal) and printed onto an activated surface A slide. MALDI-Tof spectra of the mixture and S/N values for the galactosylated compound were recorded, and a detection limit of ~5% unreacted glycan was determined.

Enzyme Expression and Purification pET30a-GalT1-His was cloned into E. coli BL21 Star™ (DE3) One Shot® (Invitrogen™) and GalT was expressed under IPTG induction. In vitro folding of GalT1 from inclusion bodies was achieved as described by Ramakrishnan et al. (Ramakrishnan et al., 2001). Recombinant GalT was purified using Histrap™ HP (1 mL) and an ÅKTA protein purifier (GE Healthcare, Uppsala, Sweden) nickel affinity column. SialT protein was expressed using GS-System™ pEE vector (Lonza, Biologics plc, Berkshire, UK) in CHO-K1 cells and cell extract was used directly for experiments. Clones from *C. elegans* (CeFuT1, CeFuT8, CeFuT6) and AgFuT6 and AtFuTA and expressed and purified as reported by Serna et al. 2011.

On-Surface Glycosyltransferase Screening

The inventors next used the glycan microarrays to investigate the in vitro specificities of glycosyltransferase enzymes.

Miniaturization of assays to a microarray format allows much higher throughput and reduced reagent consumption compared to previously described investigations using SAMDI-MS (Ban et al., Nat. Chem. Biol. 2012 8: 769-733).

(i) Enzymatic on-Surface Elongation

GalT, GalNAcT, CeFuT1, CeFuT8, CeFuT6, AtFuTA and AgFuT6 activities were analyzed on surface A and surface B slides. Slides were washed and dried before conversion analysis by MALDI-Tof. Conversion of individual glycans was assessed by integration of MS peak areas for the starting sugar and reaction product (FIG. 16).

The present invention therefore demonstrates that even tetraantennary immobilized complex N-glycans can be fully enzymatically galactosylated on a surface with high efficiency at microarray dimensions.

GalT—10 mU pure bovine GalT enzyme in 100 µL of 50 mM HEPES pH 7.2, 1 mM UDP-Gal, 5 mM MnCl$_2$, 500 mU alkaline phosphatase and 2% BSA, incubated for 72 h at 37° C. with shaking.

GalT glycosylated all compounds presenting terminal GlcNAc (GL7-GL17) highly efficiently (>80% conversion for most compounds) on both surfaces A and B.

GalNAcT—15 mg cell extract dissolved in 300 µL of cacodylate buffer (100 mM, pH 7.4) with 1 mM UDP-GalNAc, 5 mM MnCl$_2$ and 500 mU alkaline phosphatase, incubated for 72 h at 22° C. with orbital shaking.

*C. elegans* GalNAcT extract was found to extend glycans abundant in invertebrates, having both terminal GlcNAc and mannose moieties (GL14-GL17). By contrast, complex mammalian glycans GL7-GL13 were only partially glycosylated with terminal GalNAc. In certain cases, CeGalNAcT was observed to result in the formation of terminal LacdiNAc (LDN) structures, an important immunogen present in parasites and worms. The present invention may be therefore be useful in the design and/or development of vaccines and chip-based diagnostics.

FUT—*C. elegans* FuT8 displayed relatively low conversion on surface A, but highly efficient conversion on surface B for most substrates, especially for those glycan structures lacking a GlcNAc moiety on the 6 arm. This suggests that glycan surface presentation has a strong influence on accessibility and activity of CeFuT8, with the hexaethylene glycol spacer in the bidentate linker compound 2 of surface B being more permissive for core GlcNAc fucosylation. Complex glycans GL11 and GL13 were not substrates for fucosylation by CeFuT8 under the conditions employed.

Thus, the utility of having arrays in which linker type and length can be adjusted and optimized based on specific experimental requirements is demonstrated.

Both CeFuT8 and *A. gambiae* FuT6 were found only to fucosylate N-glycan structures presenting a GlcNAc moiety on the 3-arm, and to exhibit particular efficiency for fucosylation of structures having a single 3-arm GlcNAc. Additional substitution with mannose residues as in GL14-GL17 did not alter the efficiency of core fucosylation, demonstrating a clear preference of the enzyme for hybrid over complex type N-glycans.

The pauci-mannosidic compounds GL2, GL3 and GL5 were identified as substrates for the core α1,3 fucoslytransferase CeFuT1, with a conversion efficiency for a single incubation of 64-78%. These reaction products are known to be immunogenic parasite structures, further demonstrating the potential for use of the invention in vaccine development and diagnostics.

By contrast, the *Arabidopsis thaliana* homologue AtFuTA displayed similar specificity as observed for CeFuT8 and AgFuT6, catalyzing the fucosylation of all hybrid and complex type glycan structures except compounds GL11 and GL13.

(ii) on-Surface Elongation of Lewis$^X$ Type Epitopes

Formation of Lewis$^X$ type epitopes (Nguyen et al., Glycobiology. 2007 June; 17(6): 586-99) through sequential conversion by successive elongations with GalT and CeFuT6 was analyzed on surface A slides (FIG. 16, GalT+CeFuT6).

Mono—and di-fucosylation was observed for galactosylated ligands GL7_Gal-GL18_Gal (GL13_Gal not determined). Bisfucosylation of compounds presenting 2 or more terminal N-acetyl-lactosamine structures usually did not exceed 10% (GL8, GL9 and GL12). Unexpectedly, >50% bisfucosylation was observed for the mono-antennary glycan GL10; a second fucose residue had been introduced at an unknown position.

In N-glycans, fucose can be present in multiple glycosidic linkages and functional enzyme assignment using lectins is compromised by the lack of specificity for a specific linkage type. Here, the present inventions is able to use mass spectrometric fragmentation techniques to establish the substitution position of the second fucose.

(iii) On-Spot MALDI MS/MS

Regioselectivity of CeFuT6 enzyme on GL10-Gal was determined by on-chip analysis using an Ultraflextreme III Tof/Tof instrument with LIFT. Spectra were acquired by FlexControl Software in positive ionization mode with LIFT, a cell voltage of 18.9 kV and a final acceleration voltage (reflector voltage) of 29.3 kV. The parent mass ion was assigned manually (monoisotopic peak). The MS/MS spectra were acquired from 2000-3000 laser shots by adjusting the laser intensity above the threshold for desorption/ionization.

Figure 11A:
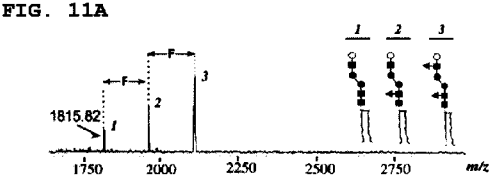
FIG. 11A-FIG. 11C. Identification of the second fucosylation site on difucosylated GL10_Gal.
Figure 11C:
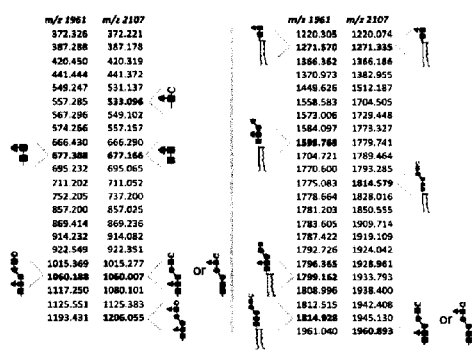
Figure 11B:
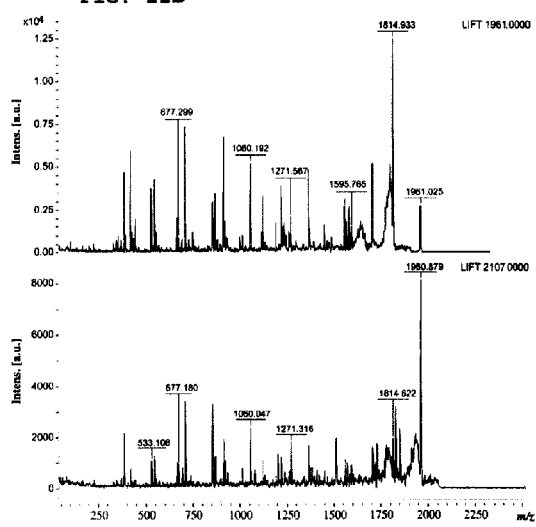

Mono- and di-fucosylated compounds were fragmented by LIFT, and despite only picomolar amounts of the glycans being available on microarray spots, the substitution position of the second fucose was unambiguously identified as the second non-reducing chitobiose unit (FIG. 11).

(iv) Enzymatic on-Surface Elongation with SialT 100 mg crude extract of recombinant SialT expressed in CHO cells was added to 50 mM of cacodylate buffer pH 6.5, 1 mM CTP-Sialic acid, 5 mM $MnCl_2$ and 500 mU alkaline phosphatase, incubated at 37° C. for 3 days. Sequential conversion by successive elongations with GalT and SialT was analyzed on surface B slides (FIG. 16, GalT+SialT). When THAP was used as a matrix, only monosialylated compounds could be observed in negative ion mode. However, analysis in positive mode by modifying sialic acids through amide formation using EDC and acetohydrazide multi-sialylated compounds could be identified and quantified. In a single cycle, up to 50% conversion was observed.

FIG. 16 demonstrates the surprising finding that enzymatic elongation and mass spectrometric analysis of N glycans was performed with similar efficiency as previously reported (Serna et al. 2010) despite miniaturization to microarray dimensions.

Example 4

Lectin Arrays

Lectin arrays are often applied as high-throughput platforms for glycoprotein analysis of pure proteins, biofluids or whole cells. However, as fluorescently tagged analytes are typically only detected using scanometric methods, the identity or composition of proteins bound to a certain lectin remains unclear.

Approaches to solve this problem such as antibody overlay, antibody sandwich arrays or methods combing separation and lectin array analysis are subject to hypothesis-bias and have limited resolving power. Here the present invention used combined scanometric and mass spectrometric readout of lectin arrays and demonstrate the ability to determine both the number and identity of proteins bound to a lectin array.

Printing Protein Arrays 0.4-0.3 mg/mL (glyco)protein solutions (Concanavalin A, ConA; WGA; and *Galanthus nivalis* agglutinin, GNA, lectins and RNAse B glycoprotein) were prepared in PBS, and 50 drops (~0.3 nL per drop) were deposited onto the surface with a dot pitch of 750×750 µm. Slides were then incubated overnight at room temperature in 90% humidity, washed with PBS, quenched with ethanolamine and dried by purging Ar. Slides were stored at −20° C.

Detection of Glycoprotein Binding and Glycoform Analysis

Figure 12:
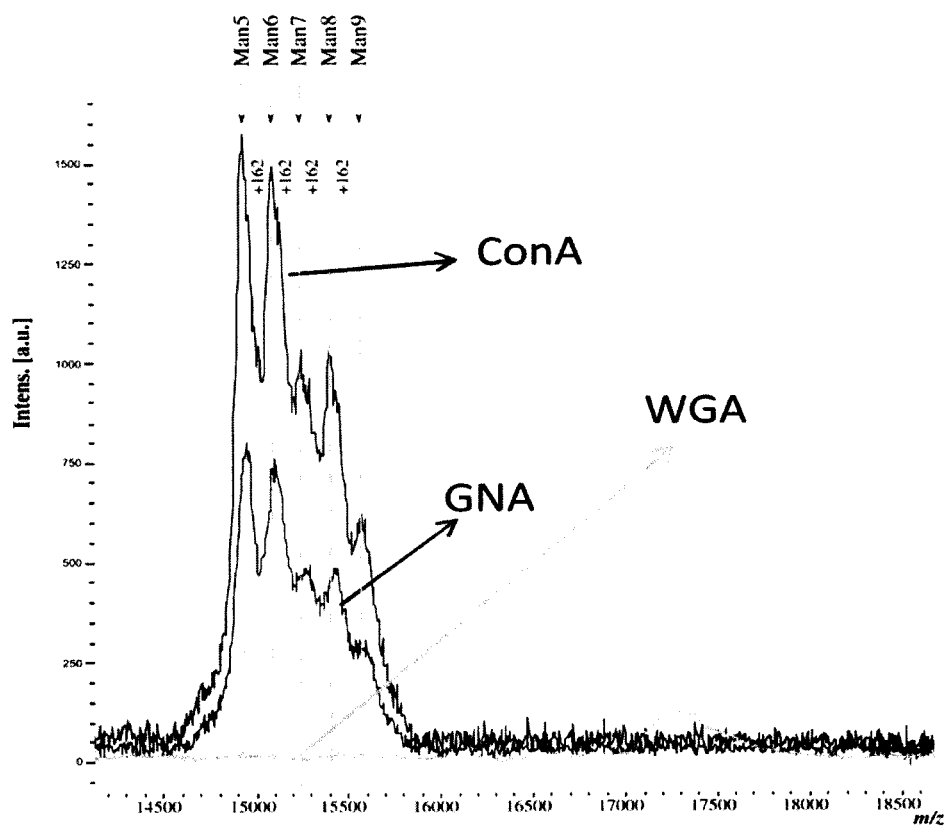
FIG. 12. MALDI-Tof spectra of RNAseB bound to ConA, WGA or GNA lectins.

A lectin array of ConA, GNA and WGA was printed onto slides as described above, and Cy3-labelled or unlabelled RNAse-B (50 µg/mL in PBS) was added to wells. RNAse B binding and lectin modifications were analyzed by fluorescence imaging and MALDI-Tof MS (FIG. 12). Fluorescence scanning showed binding of RNAse B to mannose-binding lectins ConA and GNA, but no interaction with WGA. Accordingly, analysis by MALDI-Tof MS revealed peaks for RNAse B only on ConA and GNA array spots. Furthermore, individual RNAse B glycoforms presenting the 5 mannose oligosaccharides M5-M9 were easily identified by mass differences associated with different numbers of mannose moieties (162 Da).

Detection of Glycoproteins from Complex Mixtures—Urine Glycoprotein Detection (i) Urine Processing A urine sample (17 mL) obtained from a healthy volunteer was centrifuged to remove solids and desalted by buffer exchange against PBS, yielding 0.5 mL of a concentrated protein mixture (OD ~2.0). Proteins were fluorescently labelled by 1:1 dilution in 150 mM phosphate buffer, pH 8.5 and 1 µl of Hilyte Plus™-647, for 2 h at room temperature. Labelled samples were stored after dilution with PBS to OD ~1.0.

(ii) Lectin Resin Preparation

Strong binding of low molecular weight urinary proteins to *Lens culinaris* agglutinin (LCA) has been demonstrated previously. A lectin-resin affinity support was prepared using TentaGel HL COOH (Rapp Polymere, 0.42 mmol/g) and LCA lectin. 100 mg of TentaGel resin were activated using 5 equivalents of NHS—OH and 5 equivalents of EDC for 2 h mixed with 2 mg LCA in 50 mM phosphate buffer, pH 8.7 at 4° C. overnight.

(iii) Glycoprotein Trapping and Elution

After quenching and washing, the resin was mixed with urine protein containing solution (100 µL of 1 mg/mL solution). After 1 h of incubation, the resin was washed with PBS and attached proteins were liberated using 100 mM α-methylglucose solution. MALDI-Tof MS were obtained from washed and retained protein solutions. 1 µL of resin-released solution was spotted on a MALDI plate and, using sinapinic acid, MALDI-MS spectra were obtained.

(iv) Lectin Array Assay

A lectin array was prepared as described above, including LCA lectin amongst immobilized proteins. Equivalent concentrations of proteins as in (iii) were incubated in an array, washed, dried and matrix deposited for MALDI experiments.

Figure 13:
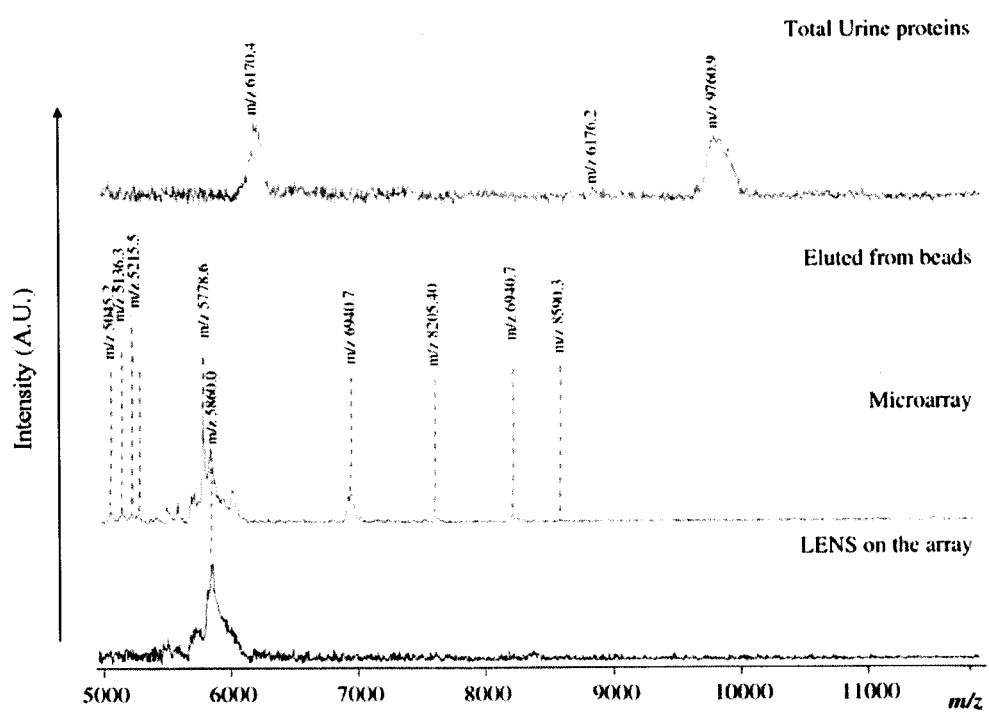
FIG. 13. MALDI-Tof spectra of low molecular weight urine proteins (5-12 kDa) in starting sample and isolated using *Lens culinaris* (LCA) bead-based suspension and LCA included in a lectin array.

FIG. 13 shows that MALDI-Tof spectra for low molecular weight urine proteins isolated using the surface protein trap or bead-based suspension assay revealed similar peptide/protein profiles, and binding of several LCA lectin binding glycoproteins. The LCA containing lectin array was particularly efficient at concentrating urine proteins presenting fucosylated glycans which were barely detectable in the starting urinary protein sample.

This demonstrates the potential for use of the present invention in diagnostics and/or prognostic monitoring. For example, low molecular weight glycoproteins such as microtubulins are known clinical markers of tubular proteinuria, and disease-related changes in their glycosylation could have prognostic value in renal pathologies.

Example 5

Lectin Identification on Glycan Arrays

Identification of proteins from complex samples by molecular mass alone is imprecise, and so the inventors investigated if on-chip tryptic protein digestion of trapped proteins followed by peptide matching could be used for unambiguous protein identification.

ConA Lectin Trapping Using Glycan Arrays

ConA—a known binder of high mannose structures—was analysed for specificity against array glycans. A surface A array containing mannosylated structures (GL3, GL4, GL5 and GL6) were prepared as described above, quenched with a 4% BSA solution and incubated with Cy-3 labelled or unlabelled ConA (40 µg/mL in PBS, 0.0005% Tween20, 2 mM $Ca^{2+}$, 2 mM $Mg^{2+}$) for 1 h. The array was then washed with PBS, dried and scanned to detect ConA-glycan interactions. Glycans GL3-GL6, GL9, GL14 and GL15 gave strong positive signal for association with ConA, and MALDI-Tof analysis of selected spots showed strong signal for the mass of the double charged ConA monomer at 13 kDa.

Tryptic Digestion on the Surface

The same slides were then warmed to 80° C. for 30 min and incubated with 10 mM iodoacetamide (IA) solution for 20 min at room temperature and dried overnight. 15 nL of trypsin (Trypsin Gold® MS Grade, 1700 U/mg, Promega) at concentrations from 0.001-0.03 µg/µL (0.25-7.6 mU) in 50 mM bicarbonate buffer, pH 7.5 with 5 mM dithiotreitol and 10 mM IA were spotted at the arrayed positions. The slide was incubated at 37° C. for 4 h in a humidity chamber, dried and 5 mg/mL solution of hydroxycinamic acid matrix (HCCA) or DHB were overspotted at the arrayed positions. MALDI-Tof and MALDI-Tof/Tof MS data were obtained for digested peptides.

Intense peaks between 1-3.3 kDa were observed for all digestion conditions on each of GL3-GL6. Comparison with a peptide mass profile for ConA digestion in solution showed a higher intensity for smaller peptide fragments and evidence for increased efficiency for on-chip digestion.

Identification of Digested Peptides (i) Identification of Parental Protein by Mascot Lists of peptide masses were transferred into the peptide mass fingerprint search program Mascot (www.matrix-science.com/cgi/search_form.p1?FORMVER=2&SEARCH=PMF) with a peptide tolerance of 0.3 KDa and an allowance for 1 missed cleavage. A search of the tryptic peptide masses on Swiss-sprot using Mascot returned Con A as the highest scoring protein (78, $p<0.05$), with 29% sequence coverage and an average MS error of 130 ppm.

(ii) Identification of Digested Peptides by MALDI-Tof/Tof

Two of the most abundant peaks of the ConA tryptic digest were subjected to on-chip peptide sequencing by MALDI-Tof/Tof (LIFT method). Assignment of fragment ions allowed reconstruction of the amino acid sequence for the 50-69aa (VSSNGSPQGSSVGR) and the 70-83aa (DLILQGDATTGTDGNLELTR) ConA tryptic peptides.

This demonstrates the potential of the present invention as platform for use in the discovery, functional and structural assignment of new lectins from complex biological matrices and for use in functional proteomics in general.

REFERENCES

All documents mentioned in this specification are incorporated herein by reference in their entirety.
Su and Mrksich, Angew. Chem. Int. Ed. 2002 41: 4715-8.
Sanchez-Ruiz et al., Angew. Chem. Int. Ed. 2011 50:1-5.
Chang et al. J. Am. Chem. Soc. 2010 132: 13371-80.
Beloqui et al. Chem. Commun. 2012 48: 1701-3.
US Patent Application No: 2010/0004137 (Mrksich et al.).
Ramakrishnan et al., J. Biol. Chem. 2001 276(40): 37665-71.
Serna et al., J. Am. Chem. Soc. 2011 133(41): 16495-502.
Serna et al., Chemistry (Weinheim an der Bergstrasse, Germany) 2010 16: 13163-75.

The invention claimed is:

1. A method of making a microarray on a surface of a solid substrate, the method comprising:
(a) providing a solid substrate having a surface for immobilizing a plurality of binding agents for forming the microarray;
(b) forming a support layer of hydrophobic molecules attached to the surface;
(c) forming a layer of linker molecules on the surface of the substrate, wherein the linker molecules comprise a hydrophobic group capable of non-covalently binding to the support layer and a reactive functional group; and
(d) printing a plurality of binding agents at a plurality of locations on the solid substrate, wherein the binding agents comprise a functional group capable of reacting in situ on the microarray with the reactive functional group of the linker molecules to covalently link the binding agents to the linker molecules immobilized on the solid substrate, thereby forming the microarray.

2. The method of claim 1, wherein the solid substrate comprises an electrically conductive material and/or an optically transparent material.

3. The method of claim 1, wherein the solid substrate comprises glass, silicon, a metal, a metal oxide or an organic polymer.

4. The method of claim 2, wherein the electrically conductive material and optically transparent material is a transparent conducting oxide, a transparent layer of a conducting metal, a transparent conducting polymer or carbon nanotubes.

5. The method of claim 4, wherein the transparent conducting oxide is selected from Indium Tin Oxide (ITO), aluminum zinc oxide (AZO), fluorine doped tin oxide (FTO) and indium doped cadmium oxide or the transparent layer of a conducting metal is gold.

6. The method according to claim 1, wherein the support layer comprises a self-assembled monolayer (SAM) of hydrophobic molecules covalently attached to the surface.

7. The method according to claim 1, wherein the method comprises an initial step of functionalizing the surface of the solid substrate so that it is capable of reacting with the hydrophobic molecules forming the support layer to covalently attach them to the substrate.

8. The method of claim 7, wherein the functionalized solid substrate surface comprises an NHS-ester, carboxylic acid, carbonate, anhydride, acyl, imidoester, sulfonyl halide, aryl, carbodiimide, aldehyde, isocyanate, isothiocyanate, epoxide, amine, oxyamine, hydrazide, thiol, cyanuric chloride, diazo, diazoalkane, conjugated diene, substituted alkene, nitrile, benzophenone, azine, diazirine, phthalamido or arylazide group for reacting with the hydrophobic molecules forming the support layer.

9. The method of claim 1, wherein the hydrophobic molecules forming the support layer comprise a hydrocarbon chain and a functional group capable of reacting with the surface of the substrate.

10. The method of claim 9, wherein the functional group of the hydrophobic molecules is an NHS-ester, carboxylic acid, carbonate, anhydride, acyl, imidoester, sulfonyl halide, aryl, carbodiimide, aldehyde, isocyanate, isothiocyanate, epoxide, amine, oxyamine, hydrazide, thiol, cyanuric chloride, diazo, diazoalkane, conjugated diene, substituted alkene, nitrile, benzophenone, azine, diazirine, phthalamido or arylazide group.

11. The method of claim 9, wherein the functional group is an NHS-ester group.

12. The method of claim 1, wherein the hydrophobic molecules of the support layer are saturated fatty acid molecules.

13. The method of claim 11, wherein the hydrocarbon chain is a saturated fatty acid molecule comprising a C10 to C36 alkyl chain.

14. The method of claim 1, wherein the support layer is formed from NHS-activated stearic acid.

15. The method of claim 1, wherein the reactive functional group of the hydrophobic linker molecules is an NHS-ester, carboxylic acid, carbonate, anhydride, acyl, imidoester, sulfonyl halide, aryl, carbodiimide, aldehyde, isocyanate, isothiocyanate, epoxide, amine, oxyamine, hydrazide, thiol, cyanuric chloride, diazo, diazoalkane, conjugated diene, substituted alkene, nitrile, benzophenone, azine, diazirine, phthalamido, arylazide or amino- oxy group.

16. The method of claim 15, wherein reactive functional group of the hydrophobic linker molecules is an NHS-ester group.

17. The method of claim 1, wherein the hydrophobic group of the linker molecules comprises a saturated alkyl chain.

18. The method of claim 1, wherein the linker molecules comprise a plurality of hydrophobic groups capable of non-covalent binding to the support layer.

19. The method of claim 18, wherein the linker molecules are bidentate.

20. The method of claim 18, wherein the hydrophobic linker molecule is represented by the structure of compound 1:

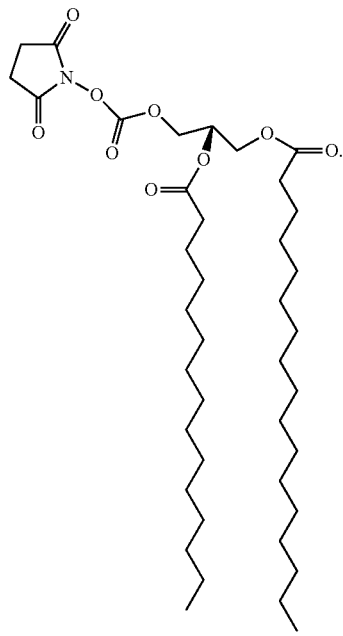 [SMILES: CCCCCCCCCCCCCCCCC(=O)OC[C@@H](COC(=O)ON1C(=O)CCC1=O)OC(=O)CCCCCCCCCCCCCC]

21. The method of claim 1, wherein the linker molecule additionally comprises a spacer moiety between the hydrophobic group and the reactive functional group.

22. The method of claim 21, wherein the spacer moiety is a polyalkylene glycol moiety.

23. The method of claim 22, wherein the hydrophobic linker molecule is represented by the structure of compound 2:

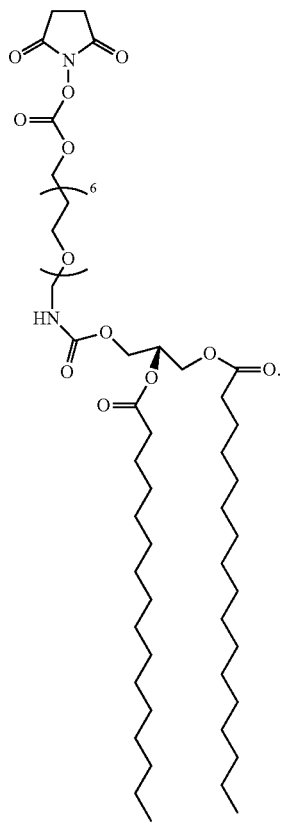

24. The method of claim 1, wherein the plurality of binding agents is or comprises a carbohydrate, protein, peptide, antibody fragment, lipid, glycoconjugate, nucleic acid or nucleic acid analog, small organic or inorganic molecule, or a, derivative, metabolite, conjugate, or hybrid thereof.

25. The method of claim 23, wherein the functional group of the plurality of binding agents capable of reacting in situ with the linker molecules is an NHS-ester, carboxylic acid, carbonate, anhydride, acyl, imidoester, sulfonyl halide, aryl, carbodiimide, aldehyde, isocyanate, isothiocyanate, epoxide, amine, oxyamine, hydrazide, thiol, cyanuric chloride, diazo, diazoalkane, conjugated diene, substituted alkene, nitrile, benzophenone, azine, diazirine, phthalamido or arylazide group.

26. The method of claim 25, wherein the functional group of the binding agent is an amine group.

27. The method of claim 1, wherein the in situ reaction of the binding agents to the linker molecules is via amide, imine, thiourea or aminoalcohol formation, or through cylcoaddition or photoimmobilization chemistries.

* * * * *